United States Patent
Togino

(10) Patent No.: US 10,653,298 B2
(45) Date of Patent: May 19, 2020

(54) OPTICAL SYSTEM, IMAGING APPARATUS, ENDOSCOPE SYSTEM, AND RANGEFINDER SYSTEM

(71) Applicant: OLYMPUS CORPORATION, Hachioji-shi, Tokyo (JP)

(72) Inventor: Takayoshi Togino, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 268 days.

(21) Appl. No.: 15/793,717

(22) Filed: Oct. 25, 2017

(65) Prior Publication Data
US 2018/0042461 A1   Feb. 15, 2018

Related U.S. Application Data

(63) Continuation of application No. PCT/JP2015/064999, filed on May 26, 2015.

(51) Int. Cl.
*A61B 1/00* (2006.01)
*G02B 17/08* (2006.01)
(Continued)

(52) U.S. Cl.
CPC ...... *A61B 1/00096* (2013.01); *G02B 17/0808* (2013.01); *G02B 17/0856* (2013.01);
(Continued)

(58) Field of Classification Search
CPC .............. G02B 17/08; G02B 17/0804; G02B 17/0808; G02B 17/0856; G02B 17/086
(Continued)

(56) References Cited

U.S. PATENT DOCUMENTS

| 6,611,282 B1 * | 8/2003 | Trubko ................. G02B 13/06 348/36 |
| 2010/0110564 A1 | 5/2010 | Togino |

(Continued)

FOREIGN PATENT DOCUMENTS

| JP | 2006276816 A | 10/2006 |
| JP | 2009015252 A | 1/2009 |

(Continued)

OTHER PUBLICATIONS

Thompson et. al. "Freeform optical surfaces: a revolution in imaging optical design", Optical express 20, 2483-99 (Year: 2012).*
(Continued)

*Primary Examiner* — Robert E. Tallman
(74) *Attorney, Agent, or Firm* — Holtz, Holtz & Volek PC

(57) ABSTRACT

The optical system is characterized by a rotationally symmetric front group that is located on a single axis of rotational symmetry passing through the center of an image plane, a rotationally symmetric back group, and an aperture, wherein the front group includes two internal reflecting surfaces and two transmitting surfaces, a light beam incident from at least one object plane on the front group forms an optical path along which the light beam enters a first transmitting surface, is reflected off a first reflecting surface and then off a second reflecting surface, and exits out of a second transmitting surface, and the light beam passes through the back group and aperture and is imaged in a position of the image plane away from the axis of rotational symmetry without being intermediately imaged within a section including the axis of rotational symmetry.

20 Claims, 18 Drawing Sheets

Example2

(51) Int. Cl.
*G02B 23/24* (2006.01)
*G02B 23/26* (2006.01)

(52) U.S. Cl.
CPC ........... *G02B 23/243* (2013.01); *G02B 23/26* (2013.01); *A61B 1/0019* (2013.01); *A61B 1/00174* (2013.01)

(58) Field of Classification Search
USPC .................... 359/642, 726–731, 733–736
See application file for complete search history.

(56) References Cited

U.S. PATENT DOCUMENTS

| | | | |
|---|---|---|---|
| 2010/0110565 A1 | 5/2010 | Togino | |
| 2011/0074917 A1 | 3/2011 | Yeh et al. | |
| 2011/0261193 A1* | 10/2011 | Agurok | F41H 13/00 348/135 |
| 2013/0057971 A1 | 3/2013 | Zhao et al. | |

FOREIGN PATENT DOCUMENTS

| | | | |
|---|---|---|---|
| JP | 2009015253 A | 1/2009 |
| JP | 2010020066 A | 1/2010 |
| JP | 4611111 B2 | 1/2011 |

OTHER PUBLICATIONS

Japanese Office Action (and English language translation thereof) dated Jun. 5, 2019 issued in counterpart Japanese Application No. 2017-520114.

International Search Report (ISR) and Written Opinion dated Jul. 28, 2015 issued in International Application No. PCT/JP2015/064999.

* cited by examiner

Example 1

Example2

Example2

Example 3

Example3

Example4

Example4

OPTICAL SYSTEM, IMAGING APPARATUS, ENDOSCOPE SYSTEM, AND RANGEFINDER SYSTEM

CROSS-REFERENCE TO RELATED APPLICATIONS

This application is based on PCT/JP2015/064999 filed on May 26, 2015. The content of the PCT application is incorporated herein by reference.

BACKGROUND OF THE INVENTION AND RELATED ART STATEMENT

The present invention relates to an optical system, an imaging apparatus, an endoscope system, and a rangefinder system, all capable of simultaneously obtaining parallax images in a plurality of base-line directions.

So far there has been an optical system disclosed for simultaneously obtaining parallax images in a plurality of base-line directions (see Japan Patent No. 4611111).

SUMMARY OF INVENTION

Optical system includes:
a rotationally symmetric front group that is located on a single axis of rotational symmetry passing through the center of an image plane,
a rotationally symmetric back group, and
an aperture, wherein:
the front group includes two internal reflecting surfaces and two transmitting surfaces,
a light beam incident from at least one object plane on the front group forms an optical path along which the light beam enters a first transmitting surface, is reflected off a first reflecting surface and then off a second reflecting surface, and exits out of a second transmitting surface, and
the light beam passes through the back group and the aperture, and is imaged in a position of the image plane away from the axis of rotational symmetry without being intermediately imaged within a section including the axis of rotational symmetry.

DESCRIPTION OF EMBODIMENTS

The optical system 1 according to one embodiment will now be explained.

Figure 1:
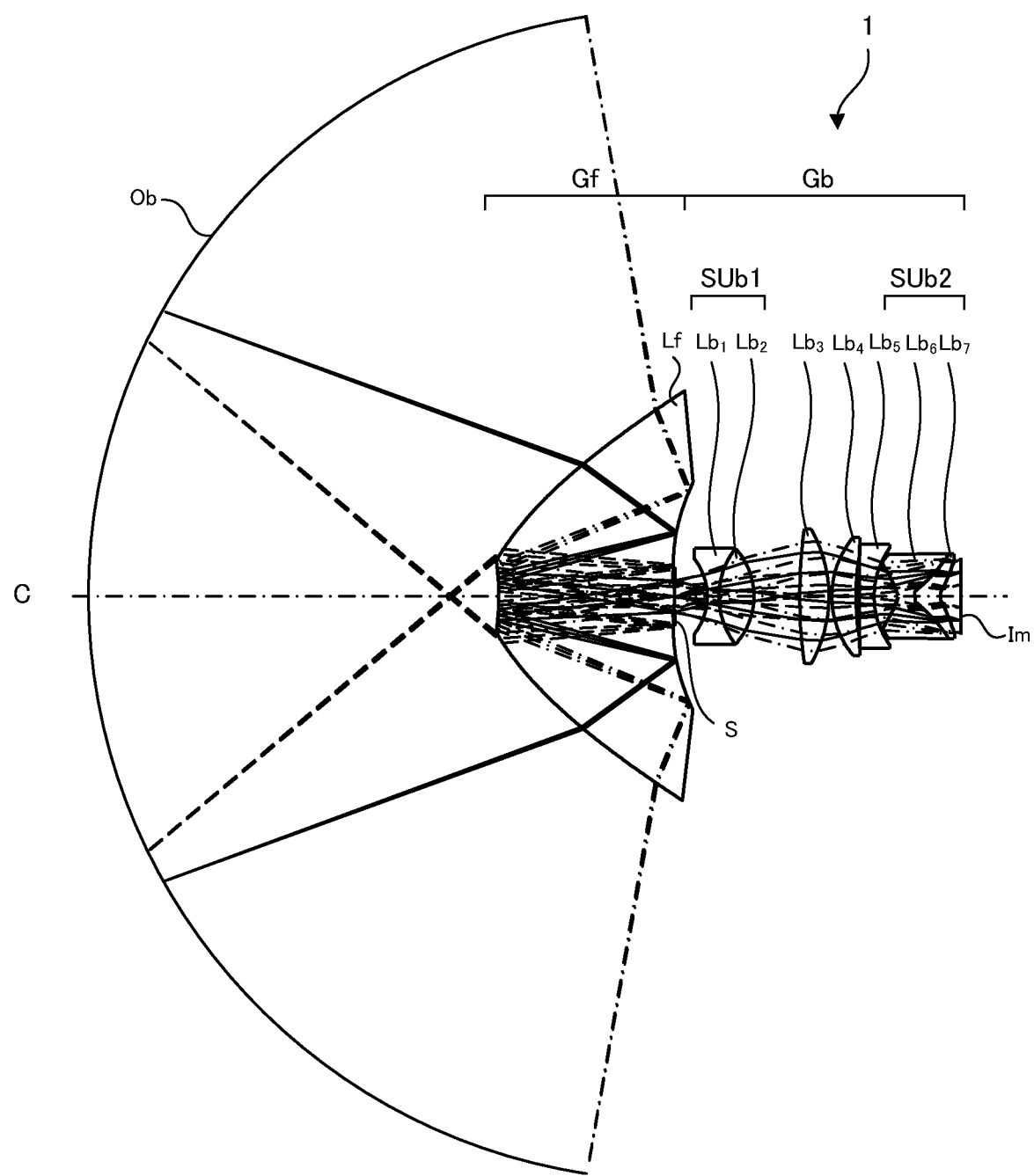
FIG. 1 is a sectional view of the optical system according to one embodiment as taken along the axis of rotational symmetry.
Figure 2:
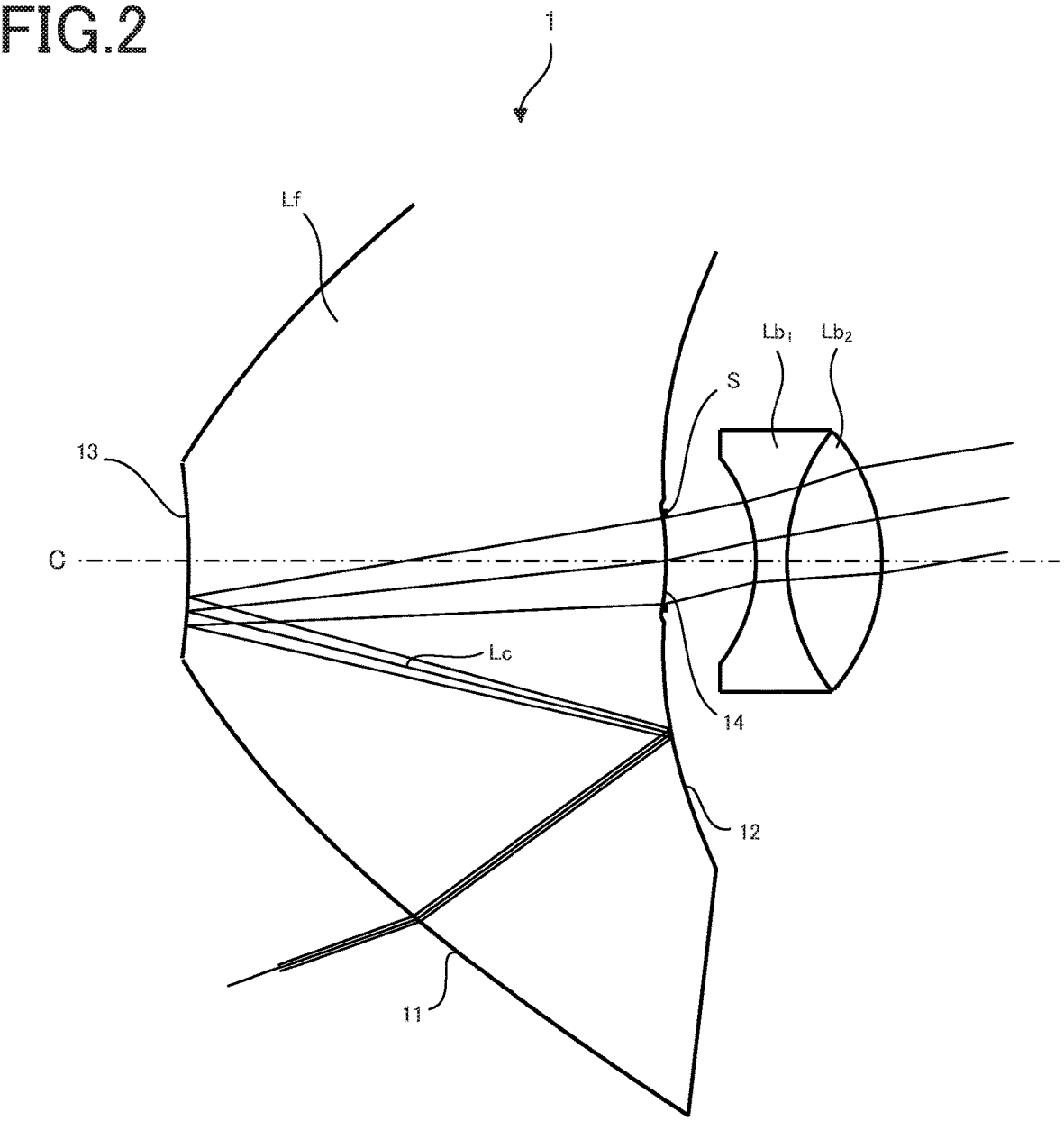
FIG. 2 is a sectional view of the optical system according to one embodiment as taken along the axis of rotational symmetry, in which the vicinity of the aperture is enlarged.
Figure 3:
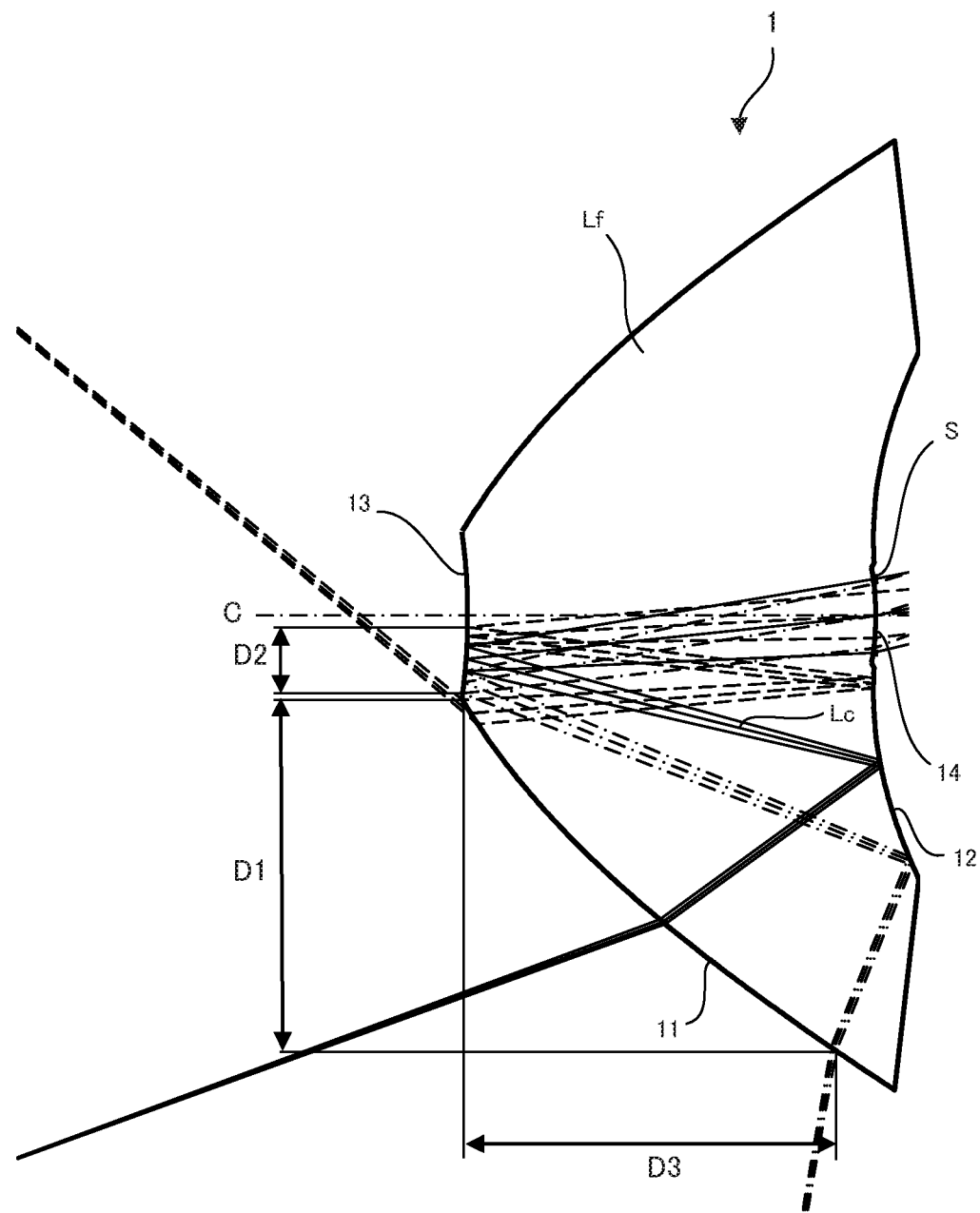
FIG. 3 is a sectional view of the front group in the optical system according to one embodiment, as taken along the axis of rotational symmetry.

FIG. 1 is a sectional view of the optical system 1 according to one embodiment as taken along the axis of rotational symmetry C. FIG. 2 is a sectional view of the optical system according to one embodiment as taken along the axis of rotational symmetry, with the vicinity of the aperture enlarged. FIG. 3 is a sectional view of the front group Gf in the optical system 1 according to one embodiment, as taken along the axis of rotational symmetry C.

The optical system 1 here includes a rotationally symmetric front group Gf that is located on a single axis of rotational symmetry C passing through the center of an image plane Im, a rotationally symmetric back group Gb including a plurality of lenses Lb1 to Lb7, and an aperture S, wherein the front group Gf includes two internal reflecting surfaces and two transmitting surfaces, a light beam incident from object plane Ob on the front group Gf forms an optical path along which the light beam enters a first transmitting surface 11 of a transparent body Lf, is reflected off a first reflecting surface 12 and then off a second reflecting surface 13, and exits out of a second transmitting surface 14, and the light beam passes through the back group Gb and aperture S, and is imaged in a position of the image plane Im away from the axis of rotational symmetry C without being intermediately imaged within a section including the axis of rotational symmetry C. Note here that a center chief ray Lc is defined by a light ray that enters the first transmitting surface 11 from the center of the observation angle of view and passes through the center of the aperture S.

In general, if the optical system 1 is set up using rotationally symmetric optical elements for all optical parts, adjustments upon setting up get easy. However, no stereoscopic images can be viewed because any parallax images cannot be formed.

In the optical system 1 here, the two reflecting surfaces of the transparent body Lf in the front group Gf forms an annular entrance pupil on the object side as an image of the aperture S. Then, a light beam exiting out of the front group Gf and having parallaxes in multiple base-line directions is imaged by the rotationally symmetric back group Gb on the image plane Im. With the optical system 1 shown in FIG. 1, it is thus possible to view an object at a portion where light beams including the axis of rotational symmetry C overlap each other as a stereoscopic image.

For stereoscopic viewing, the front group Gf is preferably made up of the transparent body Lf including the first reflecting surface 12 and the second reflecting surface 13 and capable of even-numbered reflections, because any mirror image flipped from left to right is avoidable. If the front group Gf is made up of the transparent body Lf having further a first 11 and a second transmitting surface 14 and having a refractive index greater than 1, it is then possible to form a so-called Z-shaped optical path capable of two reflections without intersecting each other so that the angle of incidence of light rays on the respective reflecting surfaces 12 and 13 can be made small. It is thus possible to reduce decentration aberrations that are introduced by oblique incidence of light rays on the reflecting surfaces 12 and 13.

The front group Gf works as a low-magnification afocal system in the sagittal plane including the axis of rotational symmetry to reduce a light beam having a wide observation angle of view from the object side down to a light beam having a narrow angle of view, which is in turn guided to the back group Gb for imaging.

Further, if the front group Gf is formed to convert a light beam without forming any intermediate image exiting out the front group Gf into a substantially parallel light beam, it is then possible to get rid of loads on the back group Gb thereby making the overall length short, because just imaging of the parallel light beam having a narrow angle of view is all that is needed for the back group Gb.

It is preferable for the optical system 1 here that the first reflecting surface 12 in the front group Gf is convex on the object side and has a negative power.

A problem with the optical system 1 designed not to project a real image of the entrance pupil in the front group Gf is that the effective diameter of the front group Gf tends to grow large at a wide observation angle of view. In other words, it is of vital importance that the first reflecting surface 12 is formed as concave surface toward the object side and has a strong negative power in the sagittal plane including the axis of rotational symmetry to convert the light beam having a wide angle of view into a one having a narrow angle of view thereby reducing the effective diameters of optical surfaces following the first reflecting surface 12. In addition, there is another effect obtained on reductions of the angle of view by allowing light rays to be incident on the medium having a refractive index of greater than 1 at the time when the light rays pass through the first transmitting surface 11. It is thus possible to keep the effective diameters of the second reflecting surface 13 and second transmitting surface 14 small and to secure a wide observation angle of view although the front group Gf is of relatively small size.

It is also preferable for the optical system 1 here that, with respect to the axis of rotational symmetry axis C in the front group Gf, the first transmitting surface 11 is located more outside than the second reflecting surface 13 and the first reflecting surface 12 is located more outside than the second transmitting surface 14.

With the first transmitting surface 11 disposed more outside than the second reflecting surface 13 with respect to the axis of rotational symmetry C, the second reflecting surface 13 may be located in the vicinity of the axis of rotational symmetry C; so the angle of incidence of a light beam on the second reflecting surface 13 is kept so small that decentration aberrations introduced by the second reflecting surface 13 can be held small.

Further, as the first reflecting surface 12 in the front group Gf is located on the outside of the second transmitting surface 14, it allows two upper and lower light beams exiting out the front group Gf to be directed toward the back group Gb with the axis of rotational symmetry C held in between while the angle between them is kept small, so the angle of view of light incident on the back group Gb becomes narrow, resulting in some considerable reductions of loads of the back group Gb on correction of aberrations.

For the optical system 1 here it is preferable that an optical path taken in the front group Gf by a center chief ray Lc incident from the center of the observation angle of view on the first transmitting surface 11 and passing through the center of the aperture S does not intersect the axis of rotational symmetry C.

It is possible to shorten the distance between a position on the first transmitting surface 11 through which the center chief ray Lc transmits and a position on the second reflecting surface 13 off which the center chief ray Lc is reflected in a direction orthogonal to the axis of rotational symmetry axis C thereby keeping the angle of incidence of the center chief ray Lc on the first reflecting surface 12 so small that decentration aberrations can be reduced.

Preferably, the optical system 1 here satisfies the following condition (1):

$$0.05 < D2/D1 < 1 \tag{1}$$

where D1 stands for the width of an effective area of the first transmitting surface 11 in a direction perpendicular to the axis of rotational symmetry C, where, there is an optical path taken by light that is incident from the object plane Ob onto the front group Gf and imaged on the image plane Im, and D2 stands for the width of an effective area of the second reflecting surface 13 in a direction perpendicular to the axis of rotational symmetry C where, there is an optical path taken by light that is incident from the object plane Ob on the front group Gf and imaged on the image plane Im.

Condition (1) is required to make the first transmitting surface 11 large and the second reflecting surface 13 small or, in another parlance, to make sure correction of field curvature and a wide observation angle of view while the effective diameter is kept small. Exceeding the upper limit to Condition (1) will cause the second reflecting surface 13 to become large and the first transmitting surface 11 to become relatively small, resulting in a failure to take hold of a wide angle for light rays and, hence, a failure to set up the optical system 1 in a wide-angle layout. Being less than the lower limit to Condition (1) will cause the second reflecting surface 13 to become too small to obtain the necessary image height, failing to form an image having good resolving power.

Preferably, the optical system 1 here satisfies the following condition (2):

$$0.2 < D1/D3 < 5 \tag{2}$$

where D1 stands for the width of an effective area where, in a direction perpendicular of the first transmitting surface 11 to the rotationally symmetric axis C, there is an optical path taken by light that is incident from the object plane Ob onto the front group Gf and imaged on the image plane Im, and D3 stands for the width of an effective area where, in a direction of the first transmitting surface 11 parallel to the rotationally symmetric axis C, there is an optical path taken by light that is incident from the object plane Ob on the front group Gf and imaged on the image plane Im.

Condition (2) relates to the tilt of the first transmitting surface 11. Exceeding the upper limit to Condition (2) will cause the tilt of the first transmitting surface 11 to get small with respect to the axis of rotational symmetry C, rendering it difficult to make the outer angle of view large. As the lower limit to Condition (2) is not reached, it will then cause the tilt of the first transmitting surface 11 to become large, resulting in a failure to make the angle of view having parallax information wide.

In the optical system 1 here, it is preferable for the first transmitting surface 11 in the front group Gf to be convex on the object side and have a positive power.

In order to make the effective diameters of the second reflecting surface 13 and second transmitting surface 14 small and make the observation angle of view wide, the first reflecting surface 12 is made up of a reflecting surface that is convex on the object side, but some considerable field curvature convex on the object side is introduced.

To correct this field curvature, it is preferable for the first transmitting surface 11 to be convex on the object side and have a positive power. This introduces a field curvature that is convex on the image side in contrast to the first reflecting surface 12 to counter the field curvature out. Further, if the first transmitting surface 11 is formed of a convex surface, it is then possible to minimize image distortion too.

In the optical system 1 here, it is preferable for at least one surface in the front group Gf to be formed of a rotationally symmetric free-form surface.

Forming at least one surface of the rotationally symmetric free-form surface makes the degree of freedom in correction of image distortion high enough to be effective for image distortion reductions. The first transmitting surface 11 in particular is preferably formed of the rotationally symmetric free-form surface.

In the optical system 1 here, it is preferable for at least one surface in the back group Gb to be formed of the rotationally symmetric free-form surface.

For correction of chromatic aberration that is introduced by the first transmitting surface 11 and become more remarkable nearer to the axis of rotational symmetry C, it is preferable to incorporate the rotationally symmetric free-form surface in the back group Gb.

Examples 1 to 4 of the optical system 1 according to the invention will now be explained with their setup parameters given later. These setup parameters are based on the results of forward or normal ray tracing from the object plane to the image plane Im via the front Gf and back group Gb as shown typically in FIG. 1.

Referring to the coordinate system for Examples 1 to 4 upon viewed in normal ray tracing, the origin O of a decentered optical surface of the decentered optical system is defined by a position of intersection of the stop surface S with the axis of rotational symmetry C, as shown typically in FIG. 1. Then, the Z-axis positive direction is defined by a direction of the axis of rotational symmetry (center axis) C that is along the direction of travel of light, and the Y-Z plane, which is a plane corresponding to the sheet plane of FIG. 1, is defined by a plane including the Z-axis and the center of the image plane Im. Then, the X-axis positive direction is defined by a direction that passes through the origin O and is orthogonal to the Y-Z plane, and the Y-axis is defined by an axis that forms a right-handed orthogonal coordinate system with the X-axis and Z-axis.

Given for a decentered surface are the quantity of decentration of the center of the surface from the origin of the optical system on a coordinate system on which that surface is defined (X, Y and Z are indicative of the X-axis direction, the Y-axis direction, and the Z-axis direction, respectively), and the angles of rotation ($\alpha$, $\beta$, $\gamma$ (°)) of the coordinate systems for defining the decentered surfaces about the X-, Y- and Z-axes, respectively. In that case, the positive signs for $\alpha$ and $\beta$ mean counterclockwise rotation about the positive directions of the respective axes (X-axis and Y-axis), and the positive sign for $\gamma$ means clockwise rotation about the positive direction of the Z-axis. Referring here to how to perform $\alpha$, $\beta$ and $\gamma$-rotations of the center axis of the decentered surface, the coordinate system that defines each surface is first rotated by angle $\alpha$ counterclockwise about the X-axis of the coordinate system that is defined at the origin of the optical system. Then, the coordinate system is rotated by angle $\beta$ counterclockwise about the Y-axis of the rotated new coordinate system. Finally, the coordinate system is rotated by angle $\gamma$ clockwise about the Z-axis of the rotated new another coordinate system.

When, of optical surfaces forming the optical system of each example, a specific surface and the subsequent surface form together a coaxial optical system, there is a surface spacing or separation given. Besides, the radius of curvature of each surface and the refractive index and Abbe number of the medium are given according to common practices.

It is here to be understood that the terms concerning aspheric surfaces with no data given in the setup parameters described later are zero. The refractive indices and Abbe numbers are given for a d-line (587.56 nm), and length is given in mm.

In this conjunction, the aspheric surface is a rotationally symmetric aspheric surface given by the following defining formula.

$$Z = (Y^2/R)/[1+\{1-(1+k)Y^2/R^2\}^{1/2}] + aY^4 + bY^6 + cY^8 + dY^{10} + \ldots \quad (a)$$

where Z is an optical axis (axial chief ray) provided that the direction of propagation of light is taken as positive, Y is a direction vertical to that optical axis, R is a paraxial radius of curvature, k is a conical constant, and a, b, c, d are the fourth-, sixth-, eighth-, tenth-order aspheric coefficients, respectively. The Z-axis in this defining formula becomes the axis of the rotationally symmetric aspheric surface.

The extended rotational free-form surface is a rotationally symmetric surface given by the following definition.

First, there is the following curve (b) given that passes on the Y-Z coordinate plane through its origin.

$$Z = (Y^2/RY)/\left[1 + \{1 - (C_1+1)Y^2/RY^2\}^{1/2}\right] + C_2Y + C_3Y^2 + C_4Y^3 + \quad (b)$$
$$C_5Y^4 + C_6Y^5 + C_7Y^6 + \ldots + C_{21}Y^{20} + \ldots + C_{n-1}Y^n + \ldots$$

Then, there is a curve F(Y) given where the curve (b) is rotated by an angle $\theta$ (°) about the X-axis with counterclockwise rotation about the X-axis positive direction rotation defined as positive. This curve F(Y), too, passes on the Y-Z coordinate plane through the origin.

That curve F(Y) is parallel translated by a distance R in the Y-axis positive direction (in the Y-axis negative direction in the case of a negative sign), and the parallel translated curve is then rotated about the Z-axis. The thus obtained rotationally symmetric surface gives an extended rotational free-from surface.

As a consequence, the extended rotational free-form surface provides a free-form surface (free-form curve) in the Y-Z plane, and a circle with a radius |R| in the X-Y plane.

From this definition, the Z-axis becomes the axis (axis of rotational symmetry) of the extended rotational free-form surface.

Here, RY is the radius of curvature of a spherical term in the Y-Z section, $C_1$ is a conical constant, and $C_2$, $C_3$, $C_4$, $C_5$, . . . are the first-, second-, third- and fourth-order aspheric coefficients, respectively.

The coordinate system will now be further explained with reference to Example 1.

Figure 4:
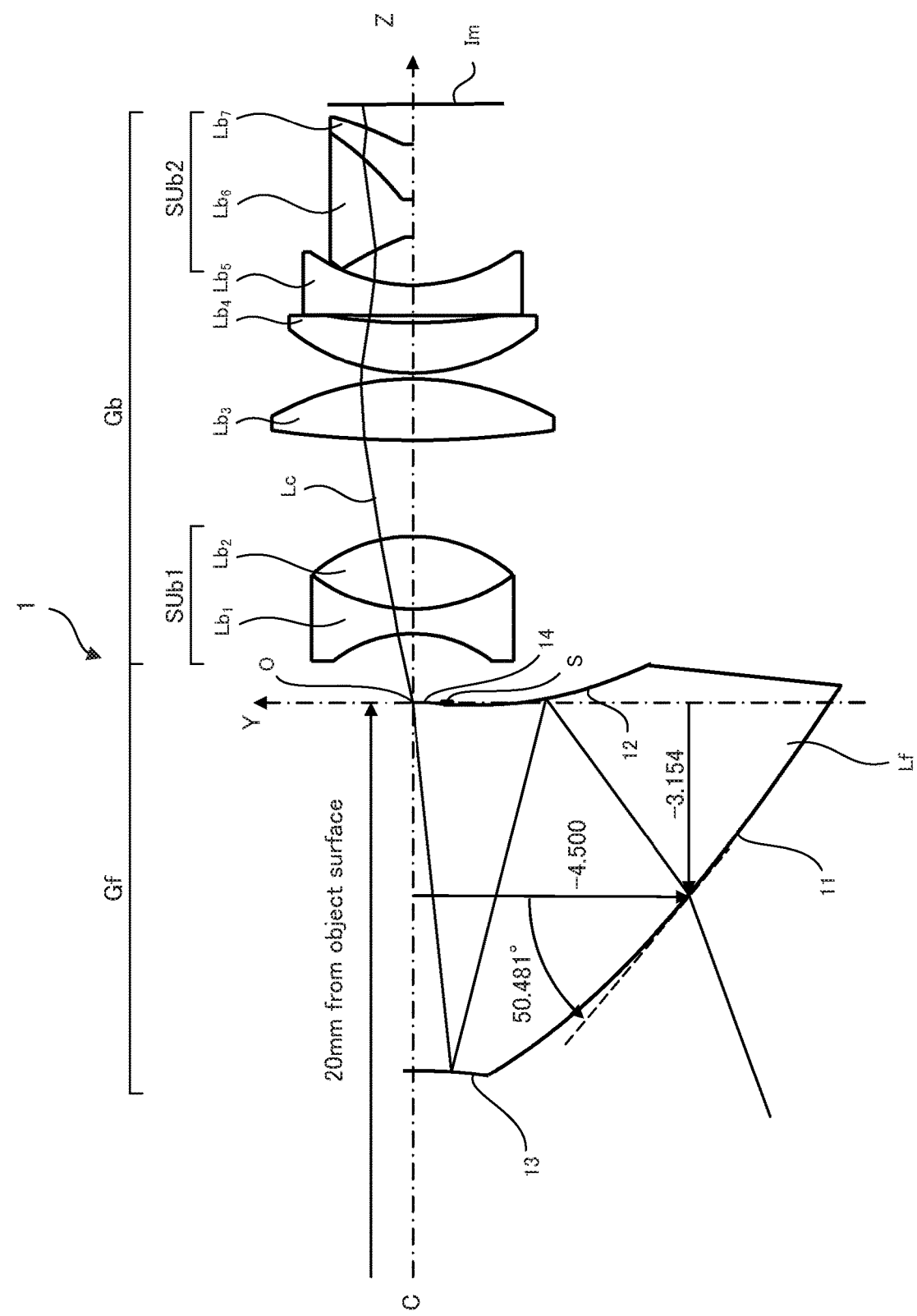
FIG. 4 is illustrative in section of one example of the coordinate system and extended rotational free-form surface in the optical system according to one embodiment.
Figure 5:
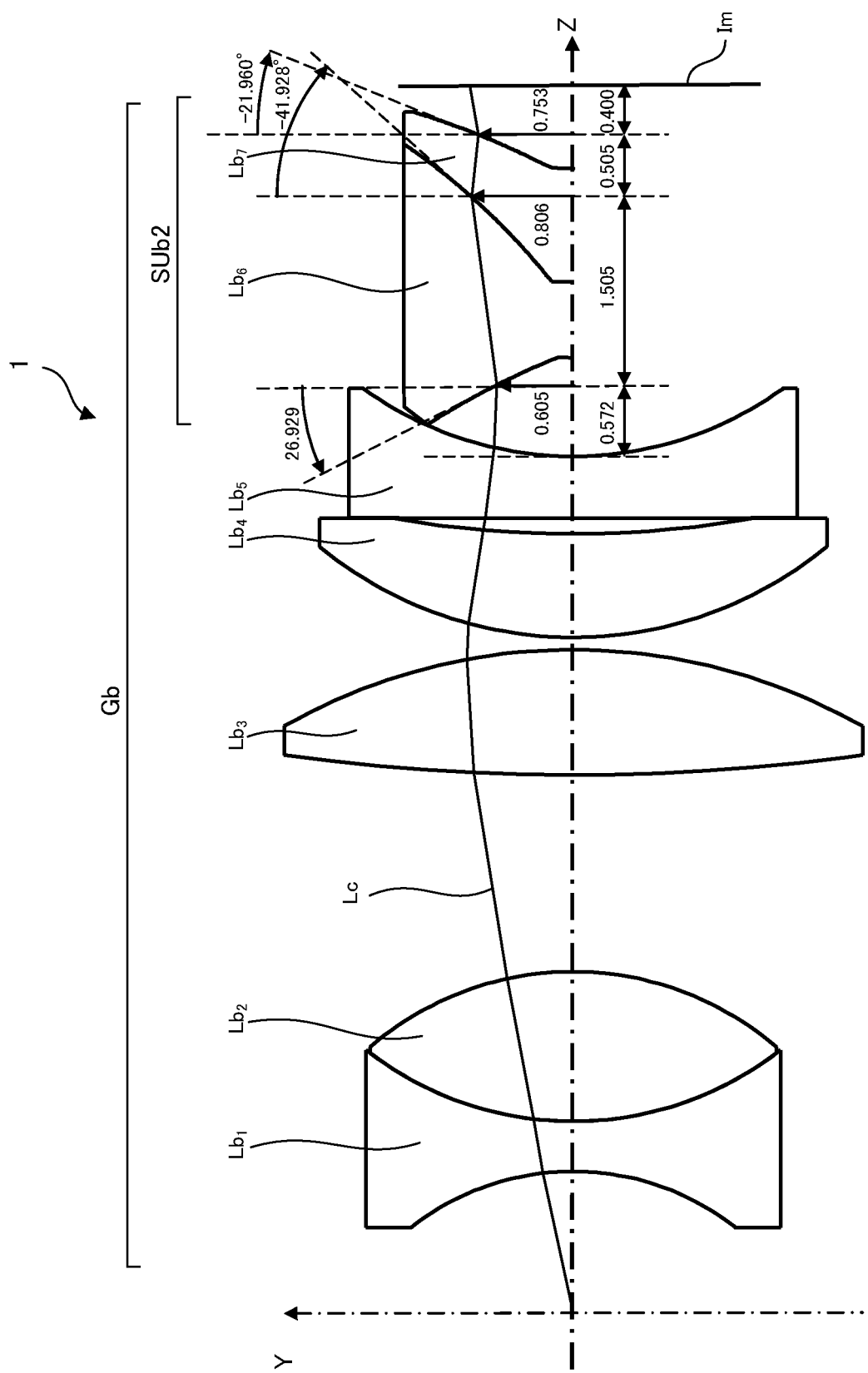
FIG. 5 is illustrative in section of one example of the coordinate system and extended rotational free-form surface in the optical system according to one embodiment.

FIGS. 4 and 5 are illustrative in section of an example for illustration of the coordinate system and extended rotational free-form surface in the optical system according to one embodiment.

In the optical system 1 described herein, all the surfaces are rotationally symmetric with respect to the single one axis of rotational symmetry axis C; in a section including the axis of rotational symmetry axis C, there are two optical paths, upper and lower. As shown in FIG. 4, however, the surface layout and optical path are explained in terms of light rays coming from below pursuant to general practices.

In this embodiment, the observation angle of view for lower light rays ranges from −40° to +80°, and for convenience of design, the center of the observation angle of view is defined by the median +20°. The center chief ray Lc is defined by a light ray that is incident on the optical system at an angle of the center of the observation angle of view and that passes through the center of the aperture, and designing is carried out with this center chief ray Lc as reference.

The surface separation of the object plane Ob is 20 mm and the surface separations of Surface Nos. 1 to 4 are all zero; that is, there is a fifth surface as a virtual surface at a distance 20 mm on the image side away from the object plane Ob. The origins of the first, second and third surface, each defined by the extended rotational free-form surface, are determined in terms of decentration from a position where the fifth surface lies.

The origin O of the first surface lies in a place given by Decentration (1) from the fifth surface, −4.500 mm down in the Y-axis direction and −3.154 mm left in the Z-axis direction, and the first surface is obliquely located at an angle of +50.481°.

The surface shape has a radius of curvature of 22.601 mm, and the C1 term tantamount to the conical coefficient of an aspheric surface is 8.2015E+0 whereas the C4 term that is the cubic term is 2.0201E−3. The first surface here is a rotationally symmetric surface obtained by rotation with the Z-axis as the axis of rotational symmetry C.

In the extended rotational free-form surface, the origin of each plane lies on the center chief ray Lc, and Decentration Y is tantamount to the height of the center chief ray Lc in the Y-axis direction. This is just a problem with designing, and may arbitrarily be determined with no need whatsoever for aligning the center chief ray Lc with the origin.

Likewise, the second surface and third surface are each formed of the extended rotational free-form surface. The fourth surface is an ordinary aspheric surface that is located in the same place as the fifth surface. The sixth surface is a stop that is located in the same position as the fourth and fifth surfaces, the position of the seventh surface is determined by the surface separation of the sixth surface, and the $8^{th}$ to $15^{th}$ surfaces are similar to those in an ordinary spherical lens system. Three image-side surfaces in the back group or the $16^{th}$ to $18^{th}$ surfaces are each formed of the extended rotational free-form surface too, and they are indicated in terms of surface separation along the Z-axis, Y-decentration, and angle of tilt α. Finally, there is a separation given between a portion of the extended rotational free-form surface on which the center chief ray Lc strikes and the image plane Im as the surface separation of the $18^{th}$ surface. In Example 1, the back group is also formed of the extended rotational free-form surface so that chromatic aberration of magnification in particular is well corrected.

In general, chromatic aberration of magnification grows large as light beam passes through a place away from the axis of rotational symmetry C and image height grows high, and is corrected by means of a cemented lens having varying Abbe number. In the optical system 1 wherein, as described herein, a light beam that is incident on the first transmitting surface 11 and has an angle of view of −40° passes through a place of the back group Gb near to the axis of rotational symmetry C, the rotationally symmetric free-form surface is used as the means for correcting chromatic aberration of magnification in the portion of the optical system that is near to the axis of rotational symmetry C and has a low image height.

Figure 6:
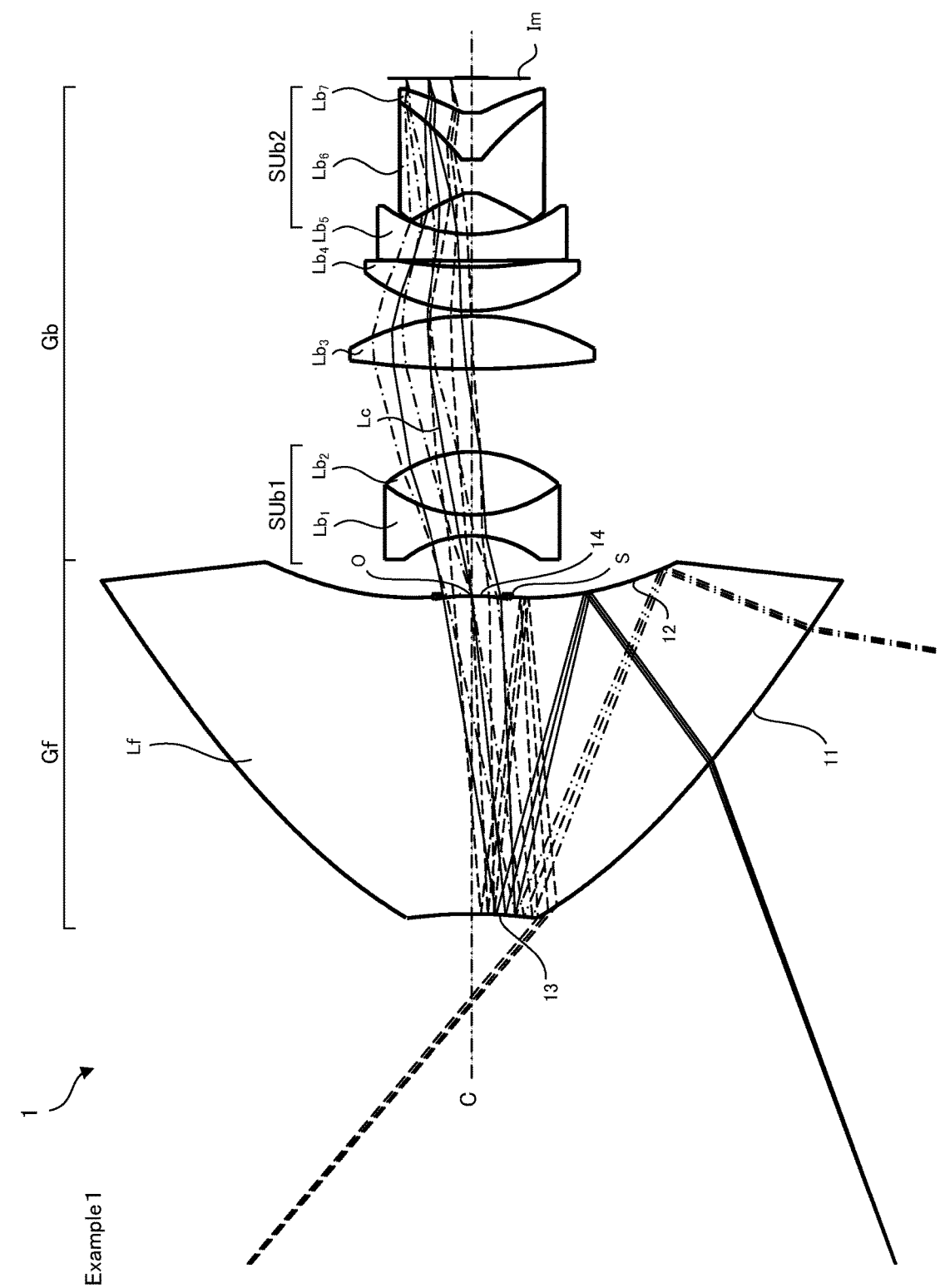
FIG. 6 is a sectional view of the optical system of Example 1 including the axis of rotational symmetry.
Figure 7:
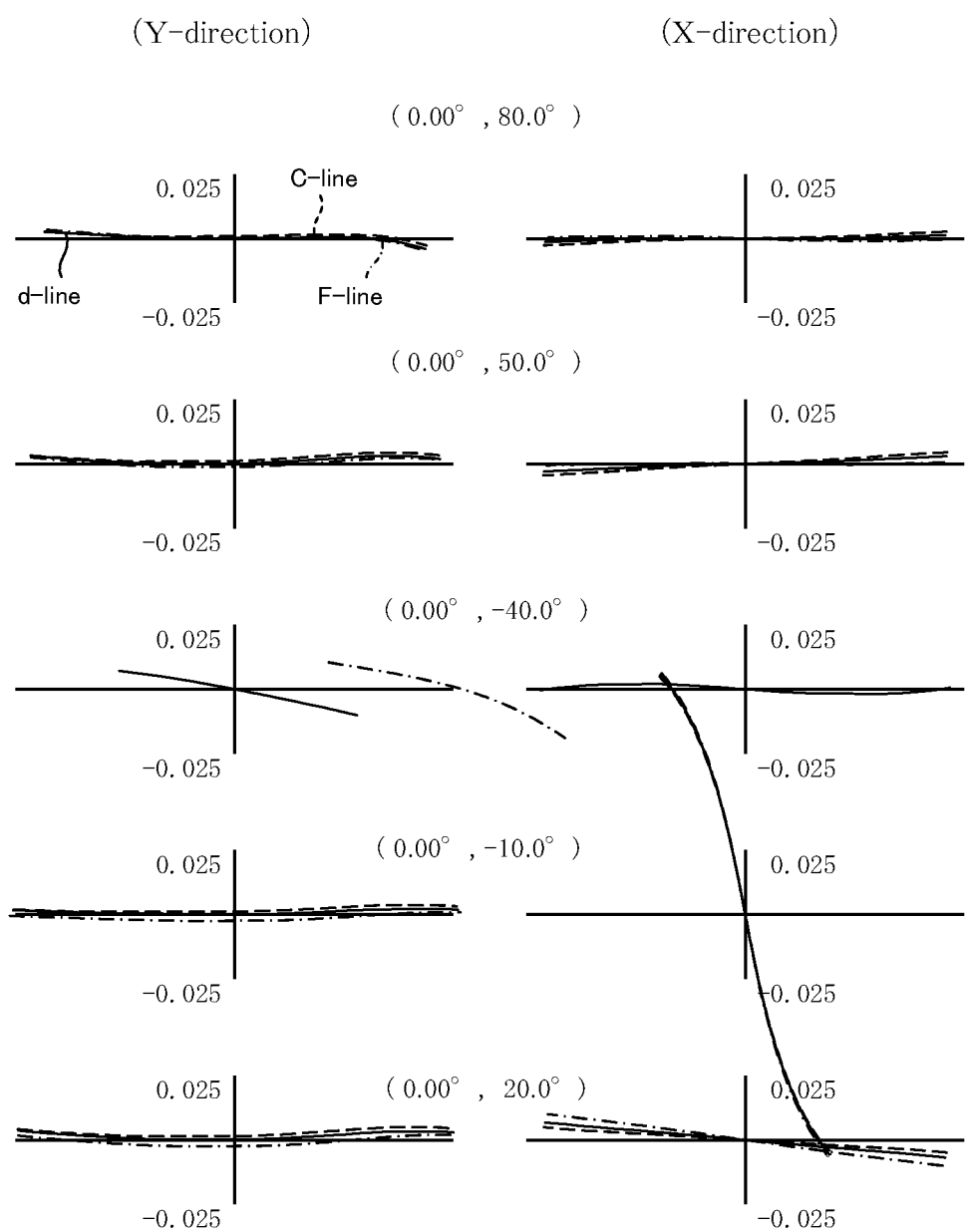
FIG. 7 is a set of transverse aberration diagrams for the optical system of Example 1.

FIG. 6 is a sectional view of the optical system 1 according to Example 1 including the axis of rotational symmetry C. Note here that only the optical path taken by light incident on one side of the center axis C in the section is shown in FIG. 6. Practically, an optical path symmetric with respect to the center axis C is also concurrently present, although not shown. FIG. 7 is a set of transverse aberration diagrams for the optical system 1 according to Example 1.

The optical system 1 according to Example 1 includes a rotationally symmetric front group Gf that is located on a single axis of rotational symmetry C that passes through the center of an image plane Im, a rotationally symmetric back group Gb and an aperture S, wherein the front group Gf includes two internal reflecting surfaces and two transmitting surfaces, a light beam incident from object plane Ob on the front group Gf forms an optical path along which the light beam enters a first transmitting surface 11, is reflected off a first reflecting surface 12 and then off a second reflecting surface 13, and exits out of a second transmitting surface 14, and the light beam passes through the aperture S and back group Gb, and is imaged in a position of the image plane Im away from the axis of rotational symmetry C without being intermediately imaged within a section including the axis of rotational symmetry C.

In Example 1, the front group Gf includes a front-group transparent body Lf. In the front-group transparent body Lf, the first transmitting surface 11 is located more outside than the second reflecting surface 13 with respect to the axis of rotational symmetry and the first reflecting surface 12 is located more outside than the second transmitting surface 14 with respect to the axis of rotational symmetry.

In the front-group transparent body Lf, the first transmitting surface 11, first reflecting surface 12 and second reflecting surface 13 each include the extended rotational free-form surface, and the second transmitting surface 14 includes an aspheric surface. On the optical path, the first transmitting surface 11 is convex on the object side and has a positive power, the first reflecting surface 12 is convex on the object side and has a negative power, the second reflecting surface 13 is convex on the image side and has a negative power, and the second transmitting surface 14 is convex on the image side and has a positive power.

In Example 1, the back group Gb includes a cemented lens SUb1 consisting of a double-concave negative lens Lb1 and a double-convex positive lens Lb2, a double-convex positive lens Lb3, a positive meniscus lens Lb4 that is convex on the object side, a negative meniscus lens Lb5 that is convex on the object side, and a cemented transparent body SUb2 in which a first back-group transparent body Lb6 either side of which is formed of the extended rotational free-form surface is cemented to a second back-group transparent body Lb7 either side of which is formed of the extended rotational free-form surface.

An optical path taken by the center chief ray Lc that is incident from the center of the observation angle of view on the first transmitting surface 11 and passes through the center of the aperture S does not intersect with the axis of rotational symmetry C in the front group Gf, intersects with the axis of rotational symmetry C at the center of the aperture S, and does not intersect with the axis of rotational symmetry C in the back group Gb.

In the optical system 1 according to Example 1, chromatic aberration of magnification is corrected at the cemented transparent body SUb2 including the extended rotational free-form surfaces in the back group Gb. In the optical system 1 according to Example 1, field curvature convex on the object side, which results from the front group Gf having reflecting surfaces, is canceled out by field curvature resulting from the back group thereby simplifying the setup of the back group.

Figure 8:
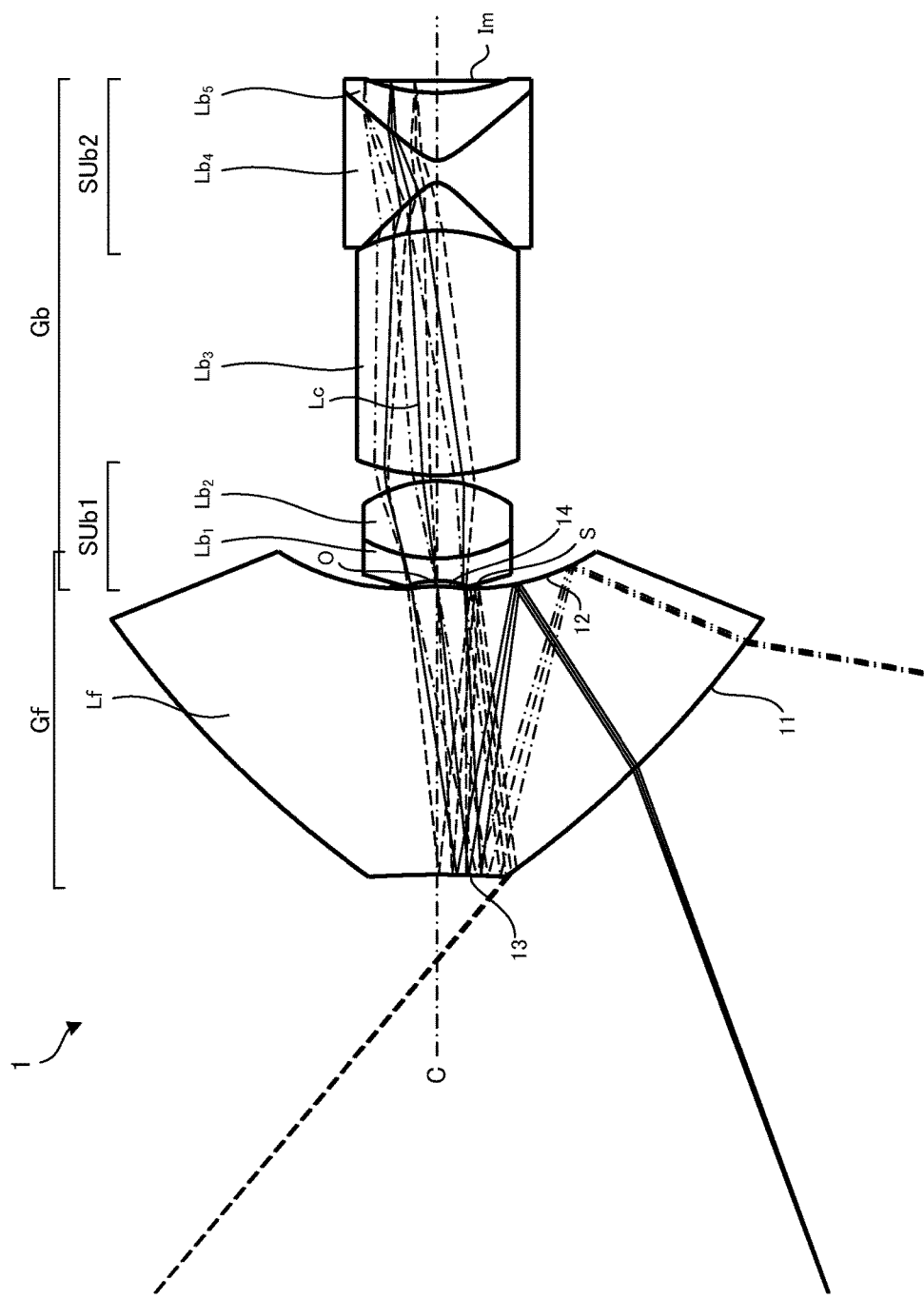
FIG. 8 is a sectional view of the optical system of Example 2 including the axis of rotational symmetry.
Figure 9:
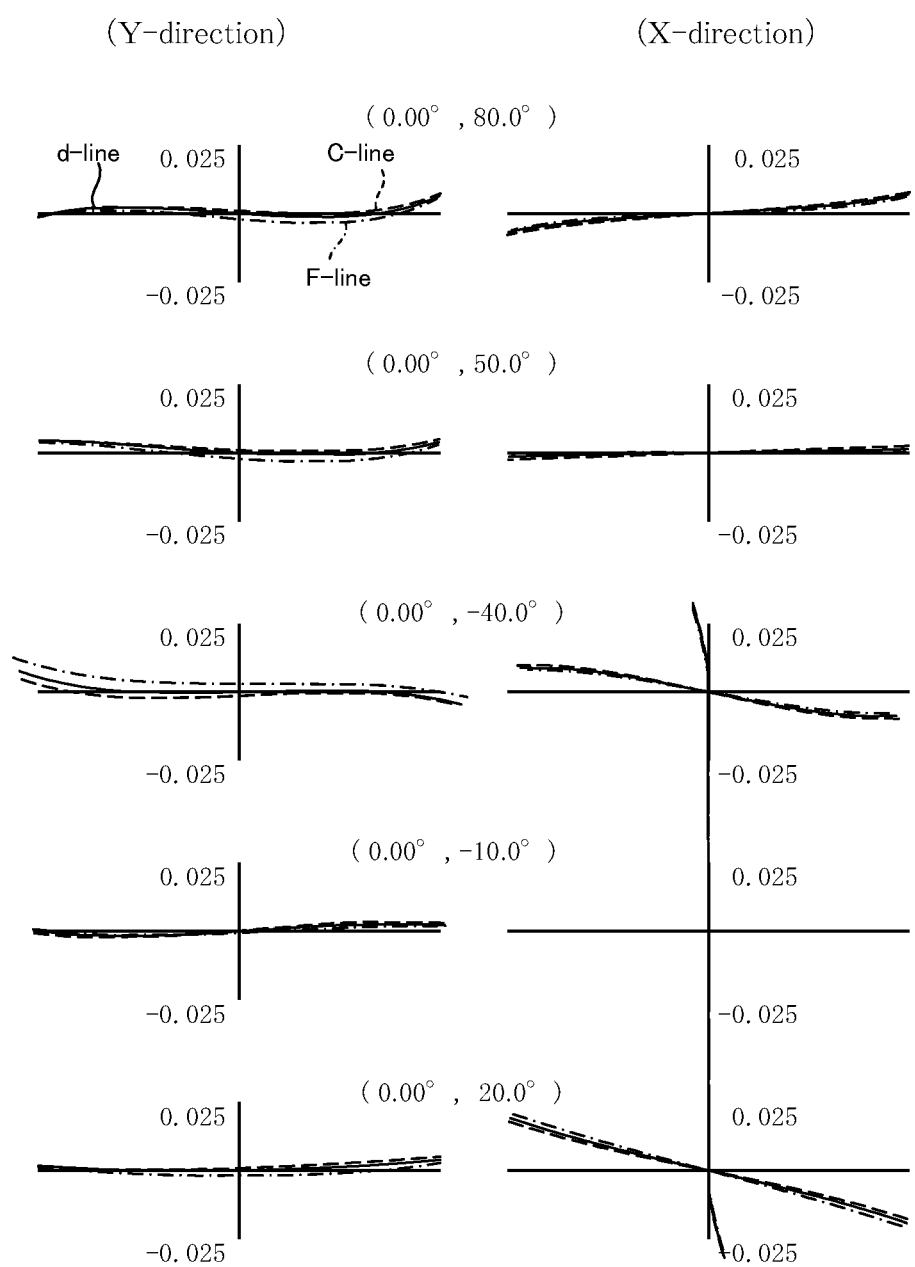
FIG. 9 is a set of transverse aberration diagrams for the optical system of Example 2.

FIG. 8 is a sectional view of the optical system 1 according to Example 2 including the axis of rotational symmetry C. Note here that only the optical path taken by light incident on one side of the center axis C in the section is shown in FIG. 8. Practically, an optical path symmetric with respect to the center axis C is also concurrently present, although not shown. FIG. 9 is a set of transverse aberration diagrams for the optical system 1 according to Example 2.

The optical system 1 according to Example 2 includes a rotationally symmetric front group Gf that is located on a single axis of rotational symmetry C that passes through the center of an image plane Im, a rotationally symmetric back group Gb and an aperture S, wherein the front group Gf includes two internal reflecting surfaces and two transmitting surfaces, a light beam incident from at least one object plane on the front group Gf forms an optical path along which the light beam enters a first transmitting surface 11, is reflected off a first reflecting surface 12 and then off a second reflecting surface 13, and exits out of a second transmitting surface 14, and the light beam passes through the aperture S and back group Gb and is imaged in a position of the image plane Im away from the axis of rotational symmetry C without being intermediately imaged within a section including the axis of rotational symmetry C.

In Example 2, the front group Gf includes a front-group transparent body Lf. In the front-group transparent body Lf, the first transmitting surface 11 is located more outside than the second reflecting surface 13 with respect to the axis of rotational symmetry and the first reflecting surface 12 is located more outer than the second transmitting surface 14 with respect to the axis of rotational symmetry.

In the front-group transparent body Lf, the first transmitting surface 11, first reflecting surface 12 and second reflecting surface 13 includes the extended rotational free-form surface. On the optical path, the first transmitting surface 11 is convex on the object side and has a positive power, the first reflecting surface 12 is convex on the object side and has a negative power, the second reflecting surface 13 is convex on the image side and has a negative power, and the second transmitting surface 14 is convex on the image side and has a positive power.

In Example 2, the back group Gb includes a cemented lens SUb1 consisting of a double-concave negative lens Lb1 and a double-convex positive lens Lb2, a double-convex positive lens Lb3, and a cemented transparent body SUb2 in which a first back-group transparent body Lb4 either side of which is formed of an aspheric surface is cemented to a second back-group transparent body Lb7 either side of which is formed of an aspheric surface.

An optical path taken by the center chief ray Lc that is incident from the center of the observation angle of view on the first transmitting surface 11 and passes through the center of the aperture S does not intersect with the axis of rotational symmetry C in the front group Gf, intersects with the axis of rotational symmetry C at the center of the aperture S, and does not intersect with the axis of rotational symmetry C in the back group Gb.

In the optical system 1 according to Example 2, chromatic aberration of magnification is corrected at the rotationally symmetric aspheric surface in the back group Gb.

Figure 10:
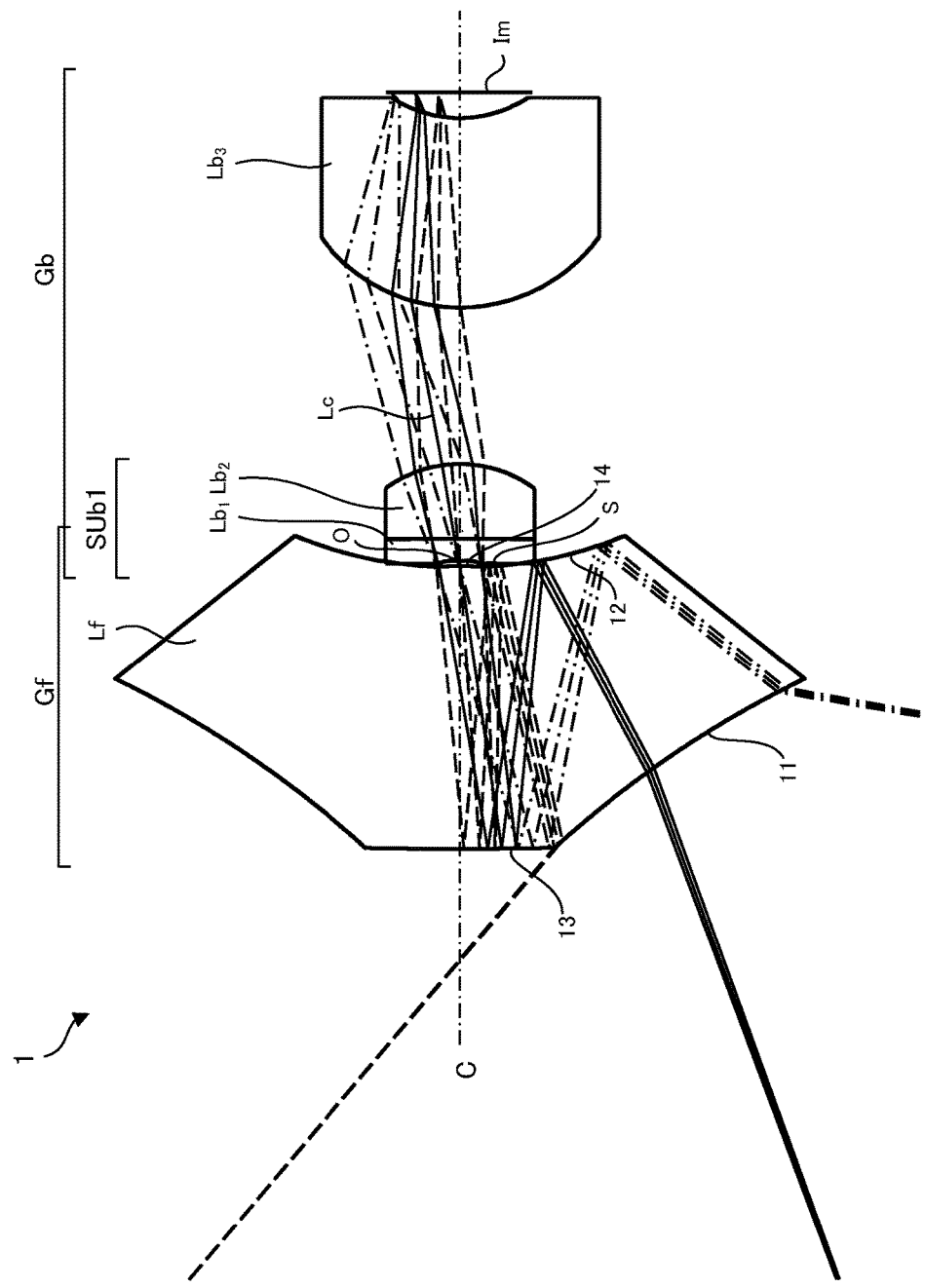
FIG. 10 is a sectional view of the optical system of Example 3 including the axis of rotational symmetry.
Figure 11:
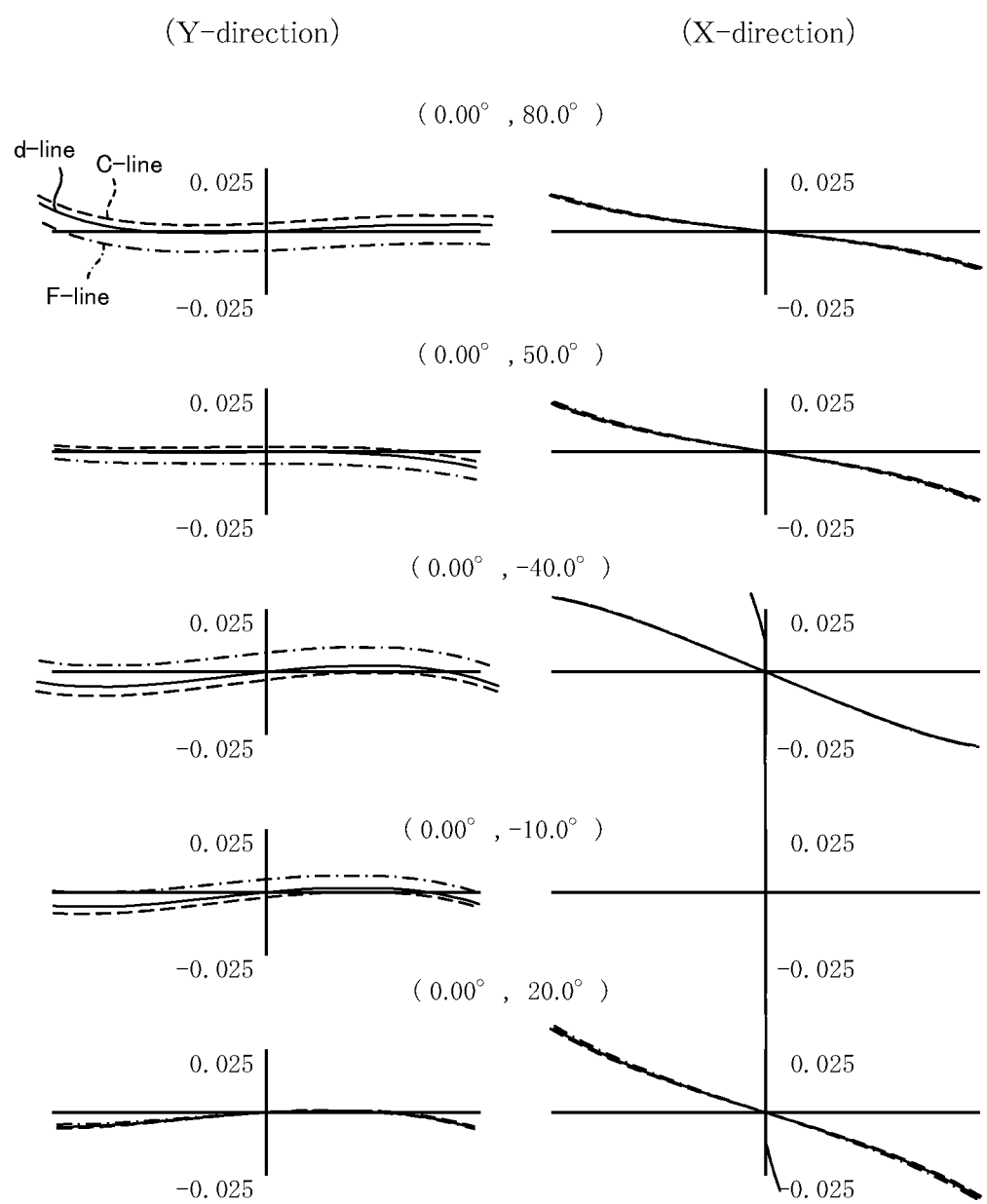
FIG. 11 is a set of transverse aberration diagrams for the optical system of Example 3.

FIG. 10 is a sectional view of the optical system 1 according to Example 3 including the axis of rotational symmetry C. Note here that only the optical path taken by light incident on one side of the center axis C in the section is shown in FIG. 10. Practically, an optical path symmetric with respect to the center axis C is also concurrently present, although not shown. FIG. 11 is a set of transverse aberration diagrams for the optical system 1 according to Example 3.

The optical system 1 according to Example 3 includes a rotationally symmetric front group Gf that is located on a single axis of rotational symmetry C that passes through the center of an image plane Im, a rotationally symmetric back group Gb and an aperture S, wherein the front group Gf includes two internal reflecting surfaces and two transmitting surfaces, a light beam incident from at least one object plane on the front group Gf forms an optical path along which the light beam enters a first transmitting surface 11, is reflected off a first reflecting surface 12 and then off a second reflecting surface 13, and exits out of a second transmitting surface 14, and the light beam passes through the aperture S and back group Gb and is imaged in a position of the image plane Im away from the axis of rotational symmetry C without being intermediately imaged within a section including the axis of rotational symmetry C.

In Example 3, the front group Gf includes a front-group transparent body Lf. In the front-group transparent body Lf, the first transmitting surface 11 is located more outside than the second reflecting surface 13 with respect to the axis of rotational symmetry and the first reflecting surface 12 is located more outside than the second transmitting surface 14 with respect to the axis of rotational symmetry.

In the front-group transparent body Lf, the first transmitting surface 11, first reflecting surface 12 and second reflecting surface 13 include the extended rotational free-form surface. On the optical path, the first transmitting surface 11 is concave on the object side and has a negative power, the first reflecting surface 12 is convex on the object side and has a negative power, the second reflecting surface 13 is convex on the object side and has a positive power, and the second transmitting surface 14 is convex on the image side and has a positive power.

In Example 3, the back group Gb includes a cemented lens SUb1 consisting of a negative meniscus lens Lb1 that is convex on the image side and a positive meniscus lens Lb2 that is convex on the image side, and a negative meniscus lens Lb3 that is convex on the object side.

An optical path taken by the center chief ray Lc that is incident from the center of the observation angle of view on the first transmitting surface 11 and passes through the center of the aperture S does not intersect with the axis of rotational symmetry C in the front group Gf, intersects with the axis of rotational symmetry C at the center of the aperture S, and does not intersect with the axis of rotational symmetry C in the back group Gb.

In the optical system 1 according to Example 3, the back group Gb is more simplified.

Figure 12:
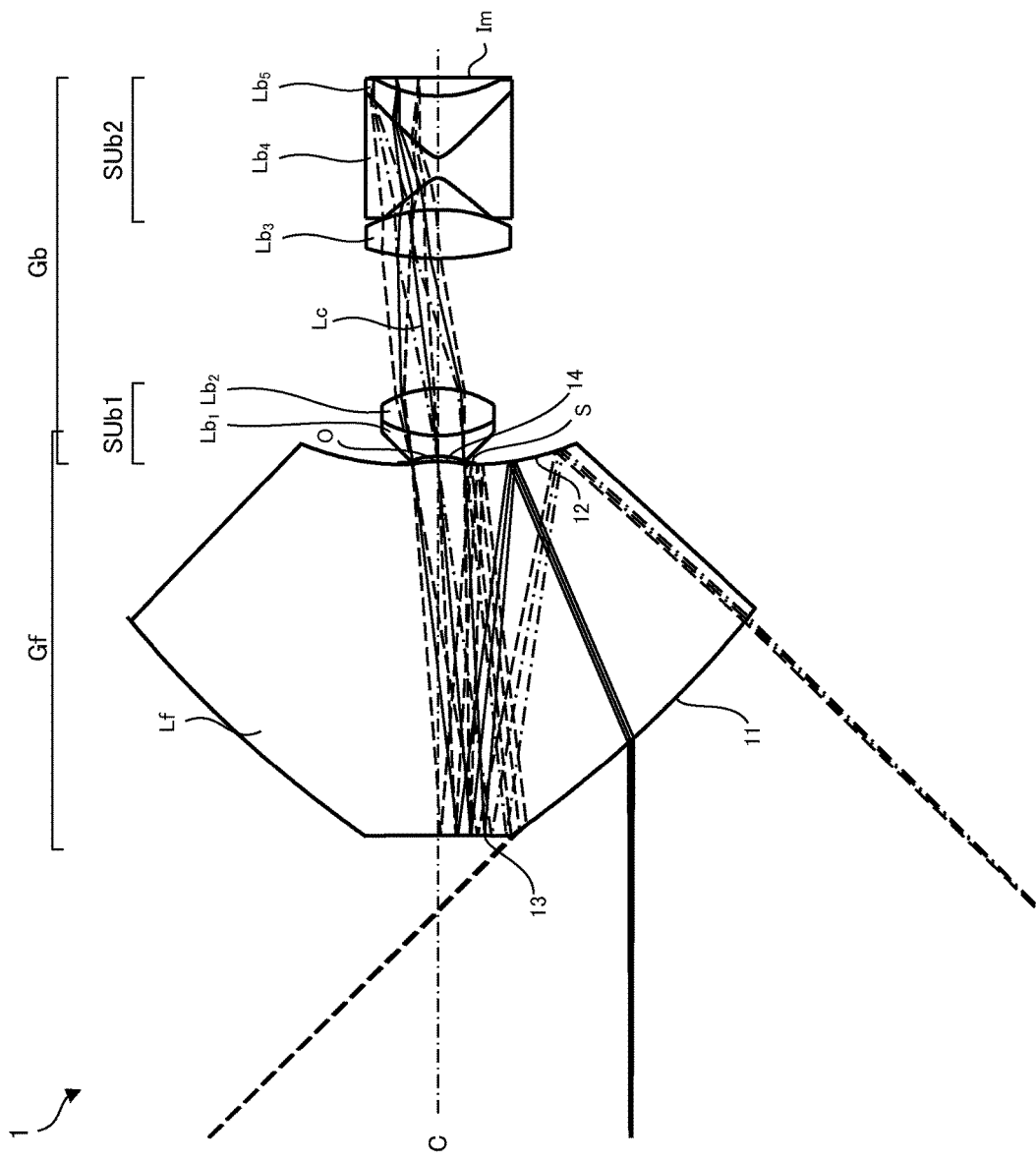
FIG. 12 is a sectional view of the optical system of Example 4 including the axis of rotational symmetry.
Figure 13:
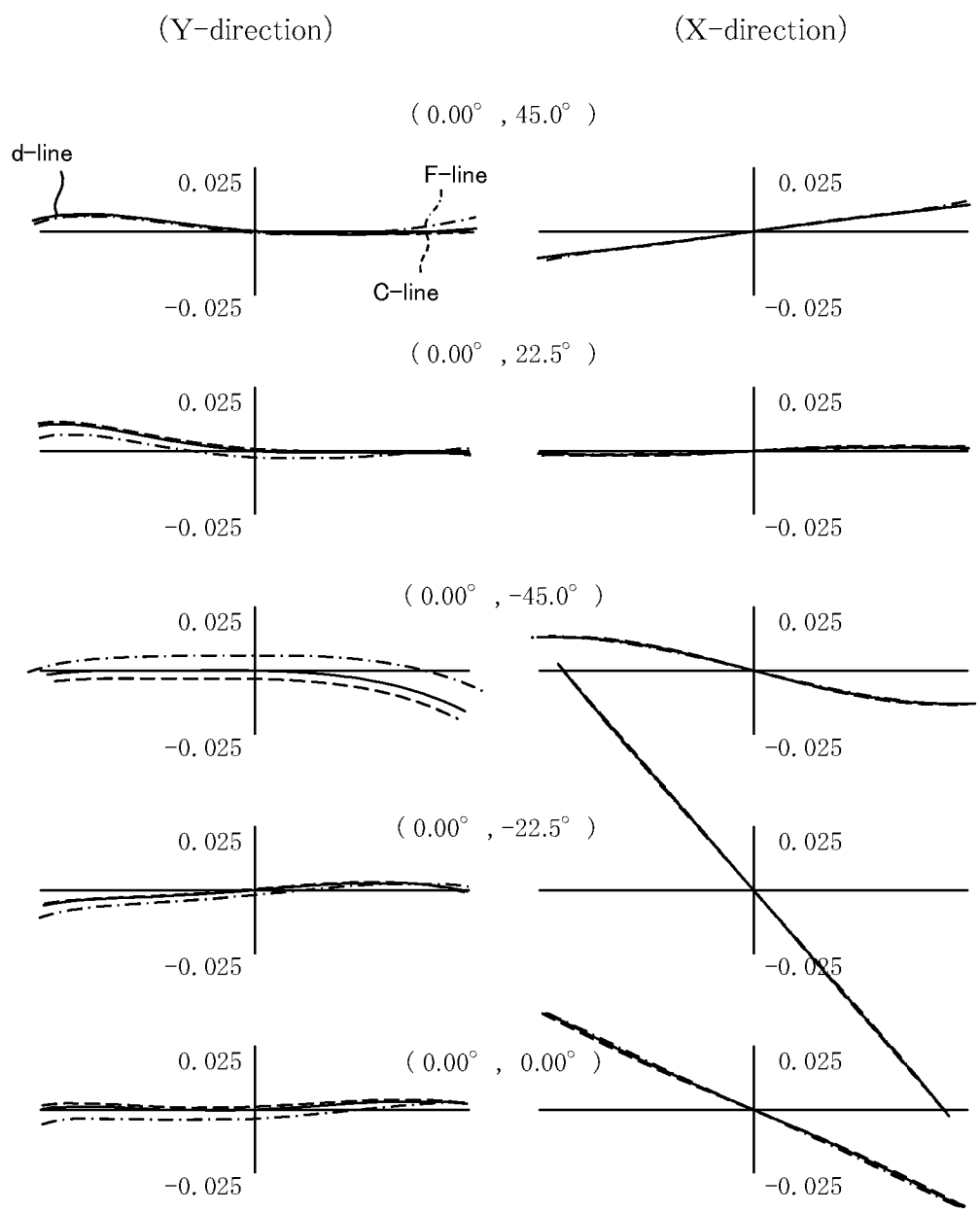
FIG. 13 is a set of transverse aberration diagrams for the optical system of Example 4.

FIG. 12 is a sectional view of the optical system 1 according to Example 4 including the axis of rotational symmetry C. Note here that only the optical path taken by light incident on one side of the center axis C in the section is shown in FIG. 12. Practically, an optical path symmetric with respect to the center axis C is also concurrently present, although not shown. FIG. 13 is a set of transverse aberration diagrams for the optical system 1 according to Example 4.

The optical system 1 according to Example 4 includes a rotationally symmetric front group Gf that is located on a single axis of rotational symmetry C that passes through the center of an image plane Im, a rotationally symmetric back group Gb and an aperture S, wherein the front group Gf includes two internal reflecting surfaces and two transmitting surfaces, a light beam incident from at least one object plane on the front group Gf forms an optical path along which the light beam enters a first transmitting surface 11, is reflected off a first reflecting surface 12 and then off a second reflecting surface 13, and exits out of a second transmitting surface 14, and the light beam passes through the aperture S and back group Gb and is imaged in a position of the image plane Im away from the axis of rotational symmetry C without being intermediately imaged within a section including the axis of rotational symmetry C.

In Example 4, the front group Gf includes a front-group transparent body Lf. In the front-group transparent body Lf, the first transmitting surface 11 is located more outside than the second reflecting surface 13 with respect to the axis of rotational symmetry and the first reflecting surface 12 is located more outside than the second transmitting surface 14 with respect to the axis of rotational symmetry.

In the front-group transparent body Lf, the first transmitting surface 11, first reflecting surface 12 and second reflecting surface 13 include the extended rotational free-form surface, and the second transmitting surface 14 includes an aspheric surface. On the optical path, the first transmitting surface 11 is convex on the object side and has a positive power, the first reflecting surface 12 is convex on the object side and has a negative power, the second reflecting surface 13 is convex on the image side and has a negative power, and the second transmitting surface 14 is convex on the image side and has a positive power.

In Example 4, the back group Gb includes a cemented lens SUb1 consisting of a double-concave negative lens Lb1 and a double-convex position lens Lb2, a double-convex positive lens Lb3, and a cemented transparent body SUb2 in which a first back-group transparent body Lb4 either side of which includes an aspheric surface is cemented to a second back-group transparent body Lb5 either side of which includes an aspheric surface.

An optical path taken by the center chief ray Lc that is incident from the center of the observation angle of view on the first transmitting surface 11 and passes through the center of the aperture S does not intersect with the axis of rotational symmetry C in the front group Gf, intersects with the axis of rotational symmetry C at the center of the aperture S, and does not intersect with the axis of rotational symmetry C in the back group Gb.

In the optical system 1 according to Example 4, chromatic aberration of magnification is corrected at the rotationally symmetric aspheric surface in the back group Gb. The optical system 1 of Example 4 has an observation angle of view of ±45°, and is capable of stereoscopic viewing at every angle of view. The center chief ray Lc is also defined by a light ray having an angle of view of zero.

Set out below are the setup or constituting parameters of the Examples 1 to 4. Note here that "ERFS" in the following tables refers to the extended rotational free-form surface.

Example 1

| Surface No. | Radius of Curvature | Surface Separation | Decentration | Refractive Index | Abbe Number |
|---|---|---|---|---|---|
| Object Surface | 20.000 | 20.000 | | | |
| 1 | ERFS[1] | 0.000 | Decentration (1) | 2.0033 | 28.3 |
| 2 | ERFS[2] | 0.000 | Decentration (2) | 2.0033 | 28.3 |
| 3 | ERFS[3] | 0.000 | Decentration (3) | 2.0033 | 28.3 |
| 4 | Aspheric Surface [1] | 0.000 | | | |
| 5 | ∞ | 0.000 | | | |
| 6 | Stop Surface | 1.138 | | | |
| 7 | −2.065 | 0.400 | | 1.7987 | 28.2 |
| 8 | 2.649 | 1.200 | | 1.7203 | 49.3 |
| 9 | −2.455 | 1.577 | | | |
| 10 | 16.739 | 1.003 | | 1.8830 | 40.7 |
| 11 | −4.613 | 0.100 | | | |
| 12 | 3.166 | 0.830 | | 1.8830 | 40.7 |
| 13 | 8.271 | 0.121 | | | |
| 14 | 219.799 | 0.500 | | 1.7279 | 24.2 |
| 15 | 2.829 | 0.572 | | | |
| 16 | ERFS[4] | 1.505 | Decentration (4) | 1.4875 | 70.4 |
| 17 | ERFS[5] | 0.505 | Decentration (5) | 1.9229 | 18.9 |
| 18 | ERFS[6] | 0.400 | Decentration (6) | | |
| Image Plane | ∞ | | | | |

-continued

| ERFS[1] |
|---|
| RDY 22.601 |
| C1 8.2015e+000  C4 2.0201e−003 |

| ERFS[2] |
|---|
| RDY 5.797 |
| C1 −2.6533e+000  C4 4.6187e−003 |

| ERFS[3] |
|---|
| RDY −9.029 |

| ERFS[4] |
|---|
| RDY −6.111 |

| ERFS[5] |
|---|
| RDY −5.401 |

| ERFS[6] |
|---|
| RDY −6.150 |

| Aspheric Surface [1] | |
|---|---|
| Radius of Curvature | −3.828 |
| k −3.6188e+000 | |

| Decentration [1] | | | | | |
|---|---|---|---|---|---|
| X | 0.000 | Y | −4.500 | Z | −3.154 |
| α | 50.481 | β | 0.000 | γ | 0.000 |

| Decentration [2] | | | | | |
|---|---|---|---|---|---|
| X | 0.000 | Y | −2.170 | Z | 0.038 |
| α | 10.907 | β | 0.000 | γ | 0.000 |

| Decentration [3] | | | | | |
|---|---|---|---|---|---|
| X | 0.000 | Y | −0.634 | Z | −6.062 |
| α | −4.044 | β | 0.000 | γ | 0.000 |

| Decentration [4] | | | | | |
|---|---|---|---|---|---|
| X | 0.000 | Y | 0.605 | Z | 0.000 |
| α | 26.929 | β | 0.000 | γ | 0.000 |

| Decentration [5] | | | | | |
|---|---|---|---|---|---|
| X | 0.000 | Y | 0.806 | Z | 0.000 |
| α | −41.928 | β | 0.000 | γ | 0.000 |

| Decentration [6] | | | | | |
|---|---|---|---|---|---|
| X | 0.000 | Y | 0.753 | Z | 0.000 |
| α | −21.960 | β | 0.000 | γ | 0.000 |

| Specifications |
|---|
| Observation angle of view: 120° (−40° to +80°) |
| Stop diameter: ϕ1.00 mm |
| Image size: ϕ0.800 to ϕ2.496 mm |

Example 2

| Surface No. | Radius of Curvature | Surface Separation | Decentration | Refractive Index | Abbe Number |
|---|---|---|---|---|---|
| Object Surface | 20.000 | 20.000 | | | |
| 1 | ERFS[1] | 0.000 | Decentration (1) | 2.0033 | 28.3 |
| 2 | ERFS[2] | 0.000 | Decentration (2) | 2.0033 | 28.3 |
| 3 | ERFS[3] | 0.000 | Decentration (3) | 2.0033 | 28.3 |
| 4 | −2.859 | 0.000 | | | |
| 5 | ∞ | −1.000 | | | |
| 6 | Stop Surface | 0.100 | | | |
| 7 | −1.510 | 0.400 | | 1.8821 | 27.4 |
| 8 | 2.693 | 1.389 | | 1.7978 | 44.4 |
| 9 | −2.190 | 0.100 | | | |
| 10 | 3.784 | 4.351 | | 1.7094 | 50.1 |
| 11 | −3.047 | 0.866 | | | |

-continued

| | | | | | |
|---|---|---|---|---|---|
| 12 | Aspheric Surface [1] | 0.400 | | 1.4875 | 70.4 |
| 13 | Aspheric Surface [2] | 1.200 | | 1.9000 | 27.1 |
| 14 | Aspheric Surface [3] | 0.200 | | | |
| Image Plane | ∞ | | | | |

ERFS[1]

RDY 19.487

ERFS[2]

RDY 4.153

ERFS[3]

RDY −20.866

Aspheric Surface [1]

Radius of Curvature −0.204
k −1.9502e+000

Aspheric Surface [2]

Radius of Curvature 0.305
k −2.3016e+000

Aspheric Surface [3]

Radius of Curvature 3.381
k 0.0000e+000

Decentration [1]

| X | 0.000 | Y | −3.500 | Z | −4.235 |
|---|---|---|---|---|---|
| α | 44.624 | β | 0.000 | γ | 0.000 |

Decentration [2]

| X | 0.000 | Y | −1.400 | Z | −0.954 |
|---|---|---|---|---|---|
| α | 11.732 | β | 0.000 | γ | 0.000 |

Decentration [3]

| X | 0.000 | Y | −0.555 | Z | −6.147 |
|---|---|---|---|---|---|
| α | −1.528 | β | 0.000 | γ | 0.000 |

Specifications

Observation angle of view: 120° (−40° to +80°)
Stop diameter: ϕ0.900 mm
Image size: ϕ0.797 to ϕ2.496 mm

Example 3

| Surface No. | Radius of Curvature | Surface Separation | Decentration | Refractive Index | Abbe Number |
|---|---|---|---|---|---|
| Object Surface | 20.000 | 20.000 | | | |
| 1 | ERFS[1] | 0.000 | Decentration (1) | 2.0033 | 28.3 |
| 2 | ERFS[2] | 0.000 | Decentration (2) | 2.0033 | 28.3 |
| 3 | ERFS[3] | 0.000 | Decentration (3) | 2.0033 | 28.3 |
| 4 | −4.267 | 0.000 | | | |
| 5 | ∞ | 0.000 | | | |
| 6 | Stop Surface | 0.100 | | | |
| 7 | −1.641 | 0.400 | | 1.8106 | 21.3 |
| 8 | −98.538 | 1.383 | | 1.8830 | 40.7 |
| 9 | −2.282 | 2.906 | | | |
| 10 | 3.149 | 3.504 | | 1.8830 | 40.7 |
| 11 | 2.255 | 0.489 | | | |
| Image Plane | ∞ | | | | |

ERFS[1]

RDY −19.710

ERFS[2]

-continued

|   |   |   |   |   |   |
|---|---|---|---|---|---|
|   | RDY 7.950 |   |   |   |   |
|   | ERFS[3] |   |   |   |   |
|   | RDY 103.054 |   |   |   |   |

| Decentration [1] | | | | | |
|---|---|---|---|---|---|
| X | 0.000 | Y | −3.500 | Z | −3.787 |
| α | 35.758 | β | 0.000 | γ | 0.000 |

| Decentration [2] | | | | | |
|---|---|---|---|---|---|
| X | 0.000 | Y | −1.438 | Z | 0.090 |
| α | 10.409 | β | 0.000 | γ | 0.000 |

| Decentration [3] | | | | | |
|---|---|---|---|---|---|
| X | 0.000 | Y | −0.767 | Z | −5.238 |
| α | 0.577 | β | 0.000 | γ | 0.000 |

Specifications

Observation angle of view: 120° (−40° to +80°)
Stop diameter: ϕ0.800 mm
Image size: ϕ0.799 to ϕ2.494 mm

Example 4

| Surface No. | Radius of Curvature | Surface Separation | Decentration | Refractive Index | Abbe Number |
|---|---|---|---|---|---|
| Object Surface | 20.000 | 20.000 |   |   |   |
| 1 | ERFS[1] | 0.000 | Decentration (1) | 2.0033 | 28.3 |
| 2 | ERFS[2] | 0.000 | Decentration (2) | 2.0033 | 28.3 |
| 3 | ERFS[3] | 0.000 | Decentration (3) | 2.0033 | 28.3 |
| 4 | Aspheric Surface [1] | 0.000 | Decentration (4) |   |   |
| 5 | ∞ | −1.000 |   |   |   |
| 6 | Stop Surface | 0.100 |   |   |   |
| 7 | −1.462 | 0.400 |   | 1.7325 | 28.2 |
| 8 | 2.230 | 0.925 |   | 1.7380 | 48.0 |
| 9 | −2.015 | 2.547 |   |   |   |
| 10 | 5.067 | 0.955 |   | 1.6653 | 31.3 |
| 11 | −3.181 | 0.638 |   |   |   |
| 12 | Aspheric Surface [2] | 0.400 |   | 1.4875 | 70.4 |
| 13 | Aspheric Surface [3] | 1.200 |   | 1.9229 | 18.9 |
| 14 | Aspheric Surface [4] | 0.353 |   |   |   |
| Image Plane | ∞ |   |   |   |   |

ERFS[1]

RDY 24.174
ERFS[2]

RDY 4.918
C1 −8.5134e+000  C4 −6.5400e−003
ERFS[3]

RDY −74.534

| Aspheric Surface [1] | |
|---|---|
| Radius of Curvature | −2.486 |
| k 0.0000e+000 | |

| Aspheric Surface [2] | |
|---|---|
| Radius of Curvature | −0.164 |
| k −2.3066e+000 | |

| Aspheric Surface [3] | |
|---|---|
| Radius of Curvature | 0.184 |
| k −1.9461e+000 | |

| Aspheric Surface [4] | |
|---|---|
| Radius of Curvature | 2.413 |
| k 0.0000e+000 | |

-continued

Decentration [1]

| | | | | | |
|---|---|---|---|---|---|
| X | 0.000 | Y | −3.750 | Z | −6.482 |
| α | 42.493 | β | 0.000 | γ | 0.000 |

Decentration [2]

| | | | | | |
|---|---|---|---|---|---|
| X | 0.000 | Y | −1.439 | Z | −1.004 |
| α | 8.362 | β | 0.000 | γ | 0.000 |

Decentration [3]

| | | | | | |
|---|---|---|---|---|---|
| X | 0.000 | Y | −0.648 | Z | −8.349 |
| α | −0.556 | β | 0.000 | γ | 0.000 |

Decentration [4]

| | | | | | |
|---|---|---|---|---|---|
| X | 0.000 | Y | 0.000 | Z | −1.000 |
| α | 0.000 | β | 0.000 | γ | 0.000 |

Specifications

Observation angle of view: 90° (−45° to +45°)
Stop diameter: ϕ1.000 mm
Image size: ϕ0.793 to ϕ2.501 mm The elements and values corresponding to Conditions (1) and (2) in the respective examples are set out in the table given just below.

| | Example 1 | Example 2 | Example 3 |
|---|---|---|---|
| D1 | 5.157 | 4.267 | 4.251 |
| D2 | 0.972 | 1.086 | 1.557 |
| D3 | 5.531 | 4.216 | 2.959 |
| Condition (1) D2/D1 | 0.188 | 0.255 | 0.366 |
| Condition (2) D1/D3 | 0.933 | 1.012 | 1.734 |

In Examples 1 to 4, the optical system 1 is designed at an object point distance of 20 mm; however, the object point distance may easily be changed to infinity or any distance by movement of the image plane position.

It is here noted that a light beam exiting out of an object point on the axis of rotational symmetry C conically enters the annular entrance pupil, passes through the optical system 1, and is imaged as a circle on the image plane Im. For this reason, the X-direction sagittal surface (the section orthogonal to the axis of rotational symmetry) of the second image height in the aberrational diagram turns in a circumferential direction, producing some considerable aberrations.

Figure 14:
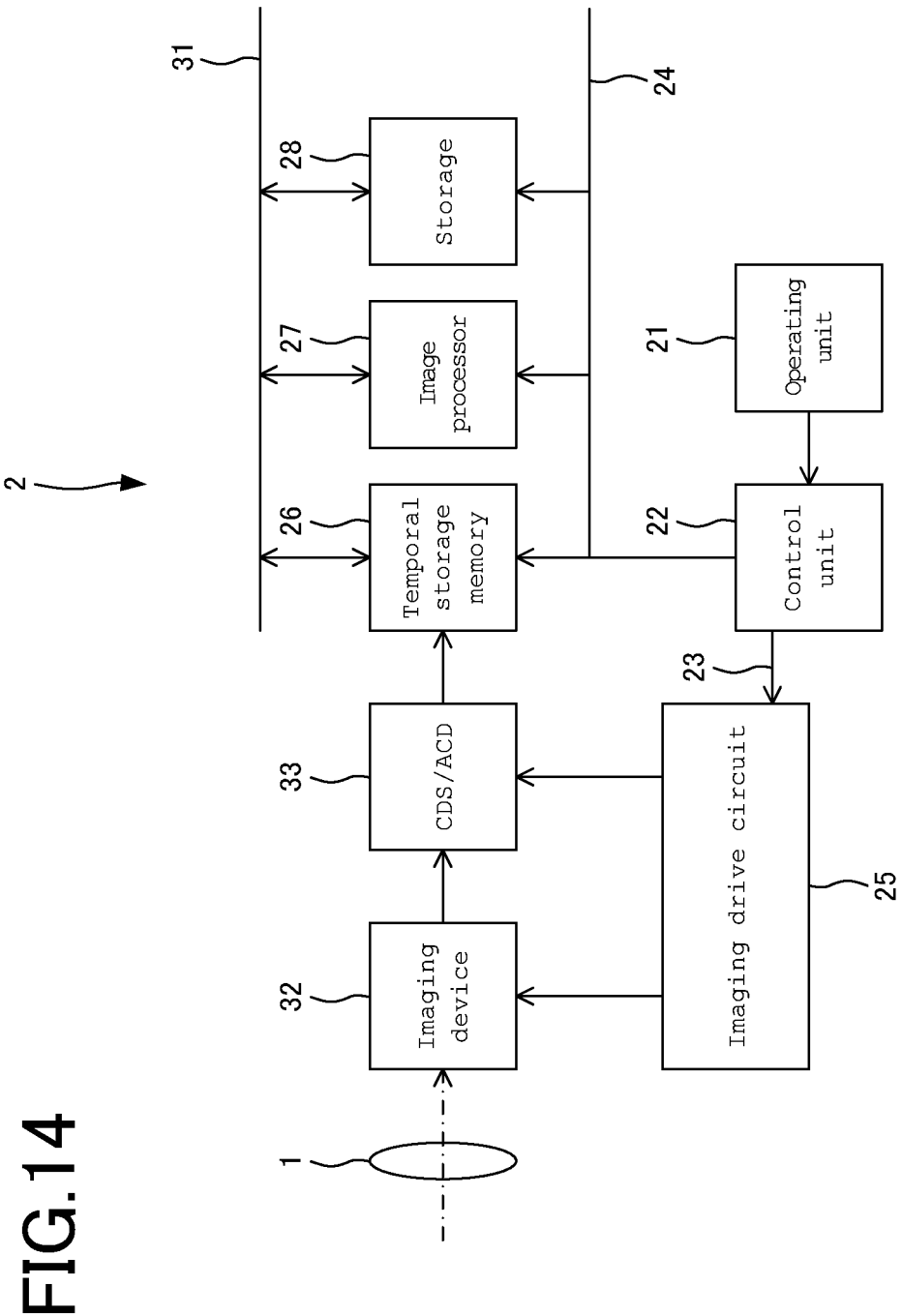
FIG. 14 is a block diagram for the internal circuit of a main part of the imaging apparatus incorporating the optical system according to one embodiment.

FIG. 14 is a block diagram for the internal circuitry of a main part of the imaging apparatus 2 to which the optical system here is applied.

As can be seen from FIG. 14, the imaging apparatus 2 includes an operating unit 21, a control unit 21 connected to the operating unit 21, an imaging drive circuit 25/temporal storage memory 26 connected to the control signal output port of the control unit 22 by way of buses 23 and 24, an image processor 27, and a storage 28.

The temporal storage memory 26, image processor 27 and storage 28 are designed such that data may be mutually input and output by way of a bus 31, and the imaging drive circuit 25 is connected with an imaging device 32 such as CCD and CDS/ADC 33.

The operating unit 21 includes various input buttons or switches, and event information entered by an operator from outside by way of them is notified to the control unit 22. The control unit 22 is typically a central processing unit (CPU) or the like, and includes a program memory (not shown) inside so that the imaging apparatus 2 is controlled on its entirety according to the program stored in the program memory.

The imaging device 32 is driven and controlled by the imaging drive circuit 25 to convert the quantity of light per pixel of an object image formed via the optical system 1 into an electric signal that is then output to the CDS/ADC 33.

The CDS/ADC 33 is a circuit in which the electric signals entered through the imaging device 32 are amplified and subjected to analog-to-digital conversion to produce the image raw data (hereinafter called the RAW data) subjected to only amplification/digital conversion processing out to the temporal storage memory 26.

The temporal storage memory 26 is a buffer including an SDRAM as an example or a memory device adapted to temporarily store the RAW data produced out from the CDS/ADC 33.

The image processor 27 is a circuit adapted to read out the RAW data stored in the temporal storage memory 26 or the RAW data stored in the storage medium 28 thereby electrically implementing a variety of image processing steps including distortion correction based on image quality parameters designated by the control unit 22.

The storage 28 includes a detachably mounted card or stick type storage medium including flash memories as an example, and the RAW data transferred from the temporal storage memory 26 or the image data processed by the image processor 27 are recorded and retained in these flash memories.

The imaging apparatus 2 set up in this way, because of incorporating the optical system 1 according to the embodiment described herein, ensures that it is of smaller size and well compatible with the taking of moving images.

Figure 15A:
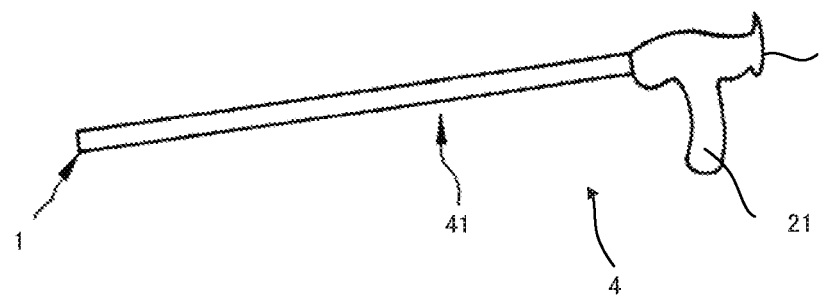
FIGS. 15A and 15B are illustrative of an endoscope system in which the optical system according to one embodiment is used as a taking optical system at the distal end of a rigid endoscope.
Figure 15B:
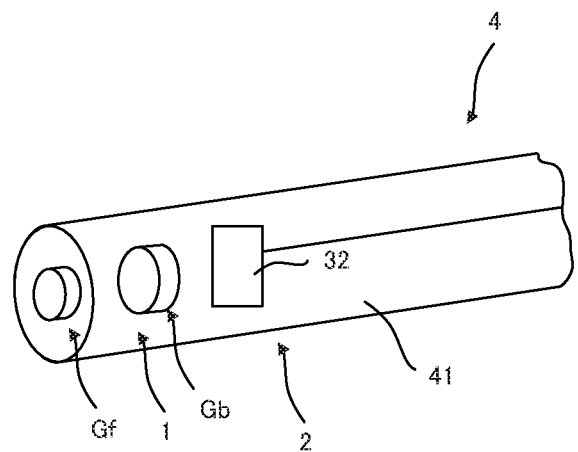

FIGS. 15A and 15B are illustrative of an endoscope system 4 in which the optical system 1 described herein is used as a taking optical system at the distal end of a rigid endoscope.

FIG. 15A is illustrative of the endoscope system 4 in which the optical system 1 described herein is attached to the distal end of an elongated portion 41a of the rigid endoscope 41 for stereoscopically taking and viewing an image, and FIG. 15B is illustrative in schematic of that distal end. The optical system 1 according to the embodiment described herein is mounted on the distal end of the rigid endoscope 4, and an imaging device 32 is positioned on the image plane of the optical system 1. In an image formed on the imaging device 32, the quantity of light is converted for each pixel into an electrical signal and then displayed on a display unit (not shown) by way of the respective electronic parts of the imaging apparatus 2 shown in FIG. 14. In other words, the endoscope system 4 includes the imaging apparatus 2 making use of the optical system 1 built in the rigid endoscope 41 as shown in FIG. 14, and the display unit (not shown). The taken RAW data, image data, operating menu and such may also be displayed on the display unit made up of a liquid crystal display monitor and the like. Note here that the main electronic parts of the imaging apparatus 2 are not necessarily incorporated in the distal end of the rigid endoscope 41; they may be incorporated in the operating unit 21 shown in FIG. 15A, a separate case or the like.

Figure 16:
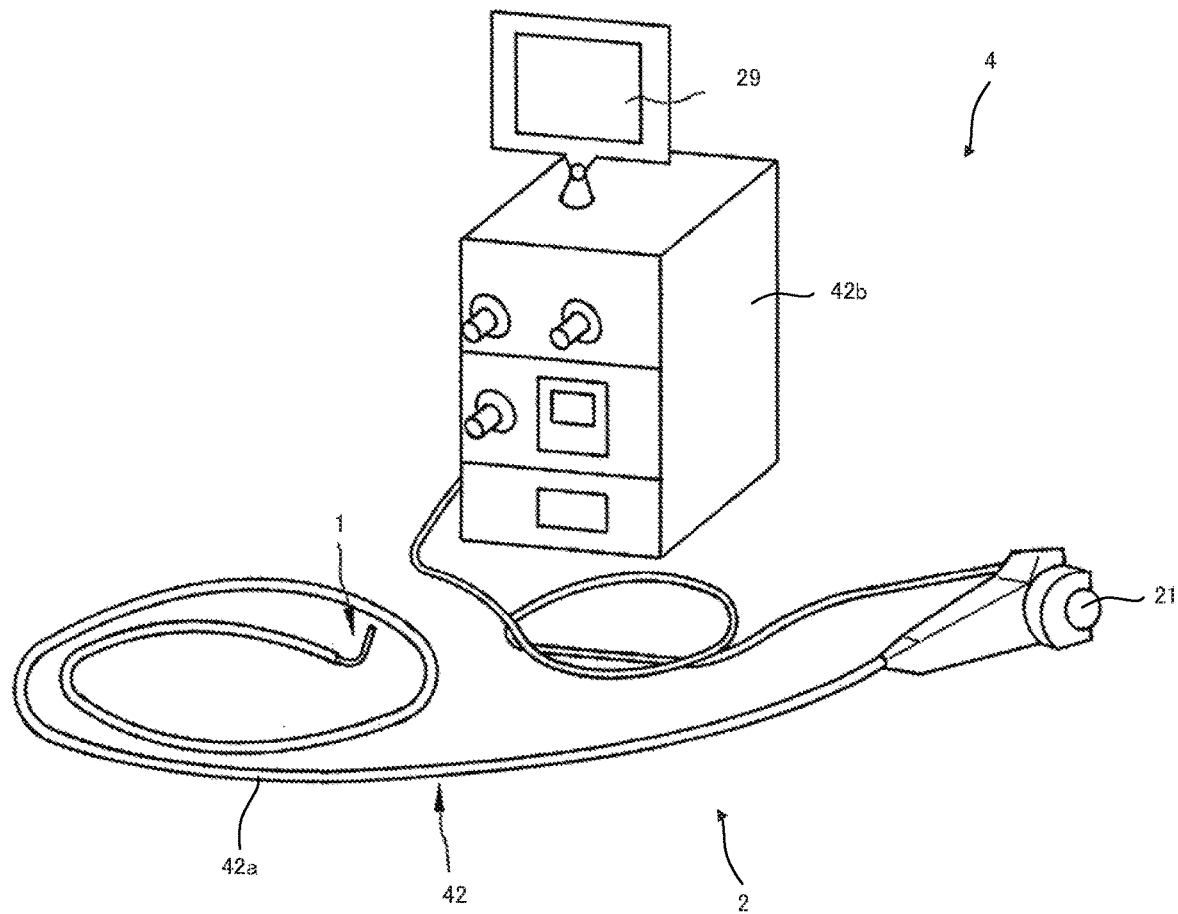
FIG. 16 is illustrative of an endoscope system in which the optical system according to one embodiment is used as a taking optical system at the distal end of a flexible endoscope.

FIG. 16 is illustrative of the endoscope system 4 in which the optical system 1 according to the embodiment described herein is used as a taking optical system at the distal end of a flexible endoscope.

In the endoscope system 4 shown in FIG. 16, the optical system 1 according to the embodiment described herein is attached to the distal end of an elongated portion 42*a* of a flexible electronic endoscope 42 so that an image formed on the imaging device 32 of FIG. 14 is stereoscopically displayed on a display unit 29 after subjected to image processing for correction of distortion. In other words, the endoscope system 4 includes the imaging apparatus 2 making use of the optical system 1 built in the flexible endoscope 42 as shown in FIG. 14, and display unit 29. The taken RAW data, image data, operating menu and such may also be displayed on the display unit 29 made up of a liquid crystal display monitor and the like. Note here that the main electronic parts of the imaging apparatus 2 are not necessarily incorporated in the distal end of the flexible endoscope 42; they may be incorporated in the operating unit 21, a separate case or the like, as shown in FIG. 16.

Thus, the endoscope system 4 includes the imaging apparatus 2 making use of the optical system 1 and display unit 29 thereby making it possible to stereoscopically take and view images. Note here that the endoscope system 4 may also take the form of a capsule endoscope in which image signals formed on the imaging device 32 through the optical system 1 received in the capsule are wirelessly transmitted to outside so that they are displayed on a display unit located on the outside of the capsule.

Figure 17A:
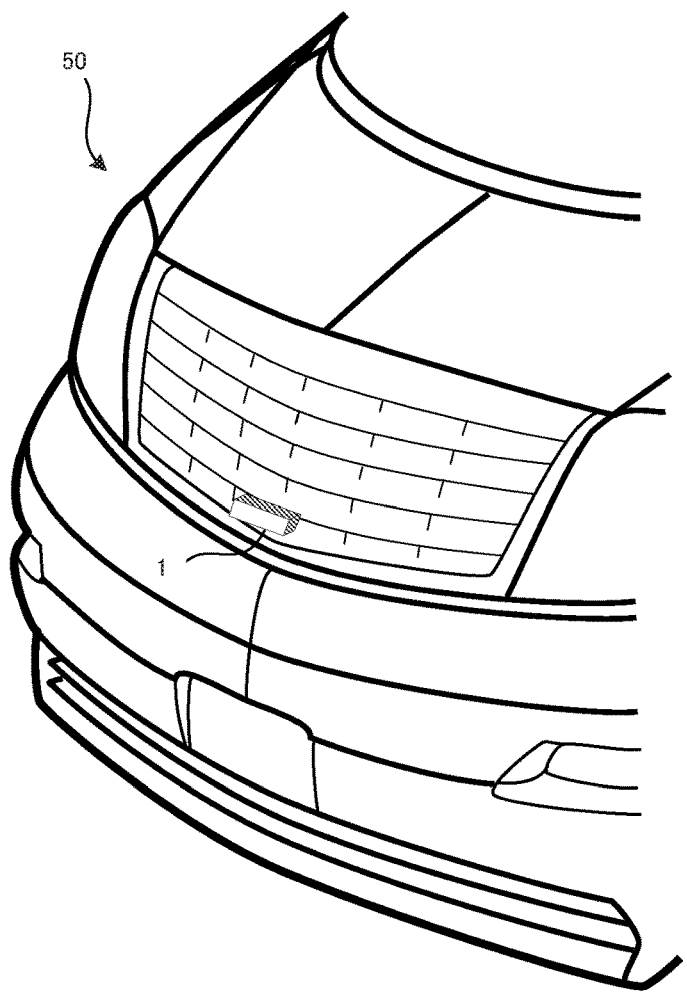
FIGS. 17A and 17B are illustrative of an example wherein the optical system according to one embodiment is used as a car's rangefinder system.
Figure 17B:
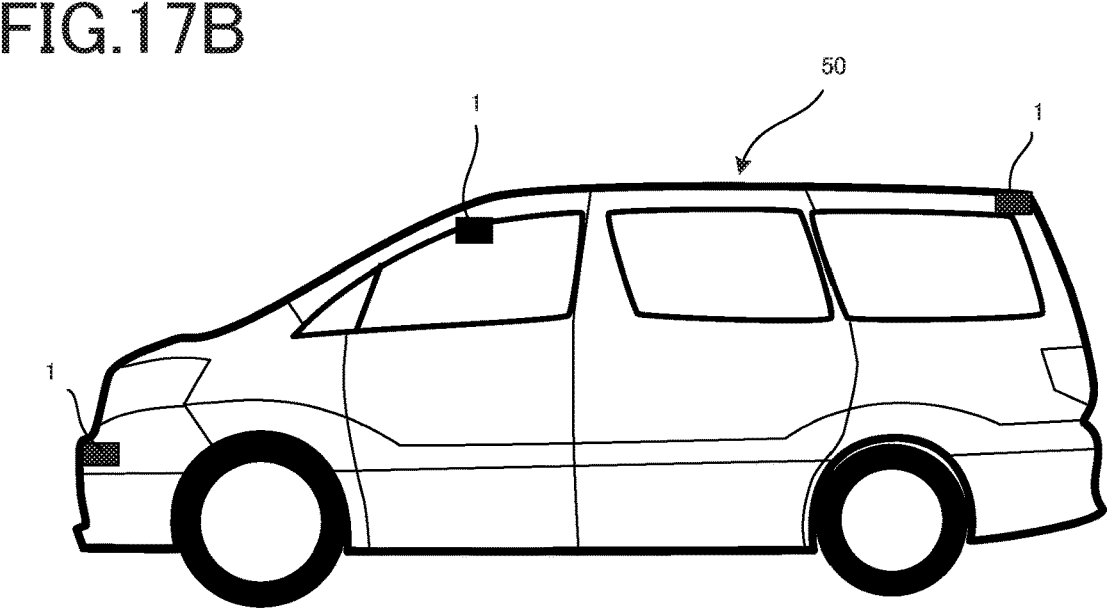
Figure 18:
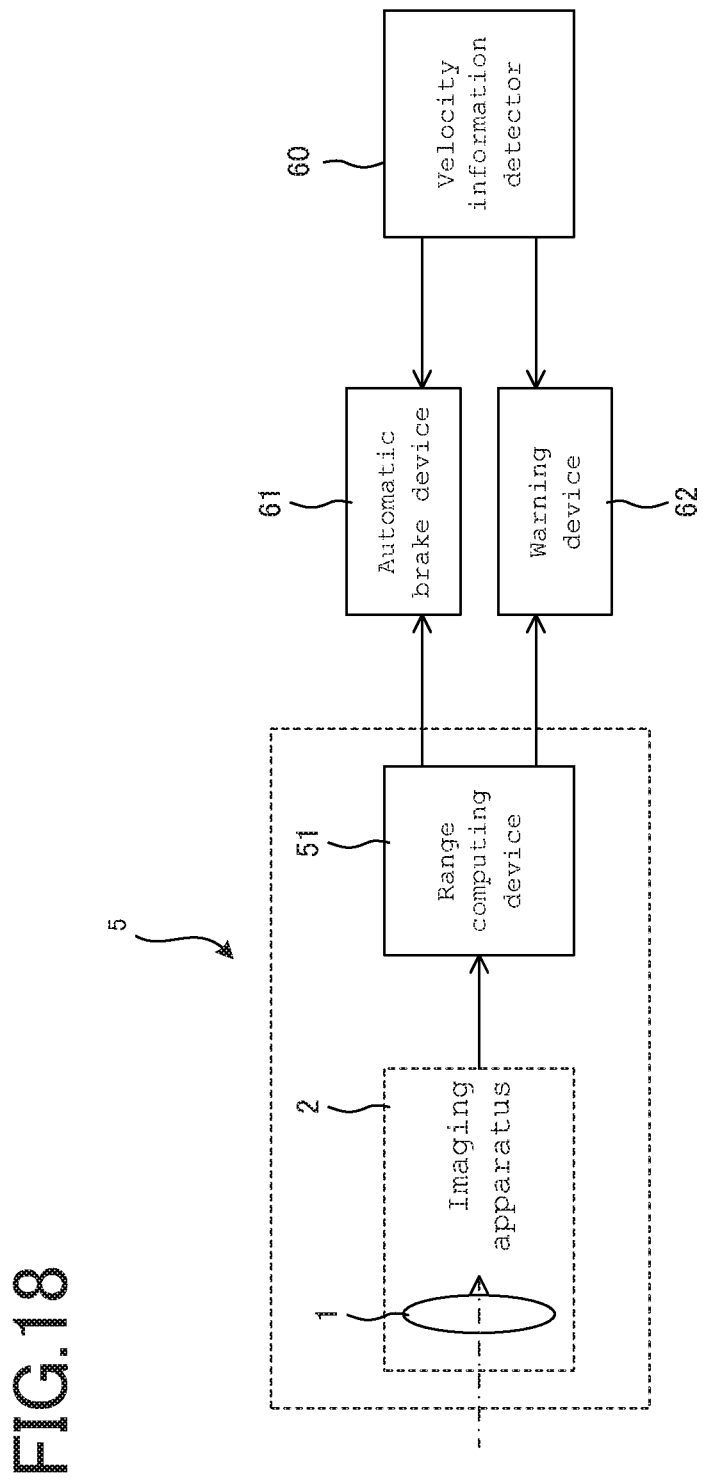
FIG. 18 is a block diagram for a rangefinder system incorporating the optical system according to one embodiment.

FIGS. 17A and 17B show an example wherein the optical system 1 according to the embodiment described herein is used as a motorcar's rangefinder system 5, and FIG. 18 is a block diagram for the rangefinder system 5 making use of the optical system 1 according to the embodiment described herein.

FIG. 17A shows an example wherein the optical system 1 of the imaging apparatus 2 according to the embodiment described herein is attached to a front portion of the car to take images ahead, and the images are corrected for distortion by image processing applied by way of the respective electronic parts as shown in FIG. 14 and then subjected to computation by a range computing device 51 shown in FIG. 18 to find a range to objects or cars in front. Images taken by way of the optical system 1 may also be displayed on an onboard display unit (not shown). In addition, the rangefinder system 5 may be applied to an automatic brake device 61 that implements automatic braking when, as judged from the relations of a distance to an object in front to the velocity, acceleration and so on determined from a velocity information detector 60, there is a risk of colliding with objects in front. Alternatively, the rangefinder system 5 may be applied to a warning device 62 that is sounded when there is a risk of colliding with an object in front.

FIG. 17B shows an example wherein a plurality of the optical systems 1 according to the embodiment described herein are attached to the corners and pole's top of a motorcar 50. In this case, too, images may be corrected for distortion by image processing applied by way of the electronic parts as shown in FIG. 14, and then subjected to computation by a range computing device shown in FIG. 18 for determination of a distance to the object. Images taken by way of the optical system 1 may be displayed on an onboard display unit (not shown) too. In addition, the rangefinder system 5 may be applied to an automatic brake device 61 that implements automatic braking when, as judged from the relations of a distance to an object in front to the velocity, acceleration and so on determined from a velocity information detector 60, there is a risk of colliding with the object in front. Alternatively, the rangefinder system 5 may be applied to a warning device 62 that is sounded when there is a risk of colliding with an object in front.

It is here to be understood that with the rangefinder system 5 making use of the imaging apparatus 2 including the optical system 1 according to the embodiment described herein, high-resolution images can be acquired; so distances or ranges to even smaller objects can also be measured.

It is here to be appreciated that the invention is in no sense limited to such embodiments as described above. While the explanation of some embodiments embraces numerous specific details for illustration, it would be obvious to those skilled in the art that diverse variations or modifications made thereto are included within the scope of the invention. In other words, illustrative embodiments of the invention are described without excluding generality from the claimed inventions and imposing any limitation thereon.

REFERENCE SIGNS LIST

1: Optical system
Gf: Front lens group
Gb: Back lens group
S: Stop
Im: Image plane

The invention claimed is:

1. An optical system comprising:
a rotationally symmetric front group that is located on a single axis of rotational symmetry passing through a center of an image plane,
a rotationally symmetric back group, and
an aperture,
wherein:
the front group includes two internal reflecting surfaces and two transmitting surfaces,
the optical system is configured such that a light beam incident on the front group from an object plane takes an optical path along which the light beam enters a first transmitting surface, is reflected off a first reflecting surface and then off a second reflecting surface, and exits out of a second transmitting surface, and
the optical system is configured such that the light beam passes through the aperture and the back group and is imaged in a position of the image plane away from the axis of rotational symmetry, and such that the light beam does not form any intermediate image within a section including the axis of rotational symmetry.

2. The optical system according to claim 1, wherein the first reflecting surface in the front group is convex on an object side and has a negative power.

3. The optical system according to claim 2, wherein, in a radial direction with respect to the axis of rotational symmetry, the first transmitting surface is located farther from the axis of rotational symmetry than the second reflecting surface, and wherein, in the radial direction, the first reflecting surface is located farther from the axis of rotational symmetry than the second transmitting surface.

4. The optical system according to claim 2, wherein an optical path taken in the front group by a center chief ray incident on the first transmitting surface from a center of an observation angle of view and passing through a center of the aperture only intersects with the axis of rotational symmetry at the center of the aperture.

5. The optical system according to claim 1, wherein the following condition (1) is satisfied:

$$0.05 < D2/D1 < 1 \qquad (1),$$

where:

D1 is a width of an effective area of the first transmitting surface in a direction perpendicular to the axis of rotational symmetry where there is an optical path taken by light that is incident from the object plane onto the front group and imaged on the image plane, and D2 is a width of an effective area of the second reflecting surface in a direction perpendicular to the axis of rotational symmetry where there is an optical path taken by light that is incident from the object plane on the front group and imaged on the image plane.

6. The optical system according to claim 1, wherein the following condition (2) is satisfied:

$$0.2 < D1/D3 < 5 \qquad (2),$$

where:

D1 is a width of an effective area of the first transmitting surface in a direction perpendicular to the axis of rotational symmetry where there is an optical path taken by light that is incident from the object plane onto the front group and imaged on the image plane, and D3 is a length of an effective area of the first transmitting surface in a direction parallel to the axis of rotational symmetry where there is an optical path taken by light that is incident from the object plane on the front group and imaged on the image plane.

7. The optical system according to claim 5, wherein the following condition (2) is satisfied:

$$0.2 < D1/D3 < 5 \qquad (2),$$

where:

D1 is the width of the effective area of the first transmitting surface in the direction perpendicular to the axis of rotational symmetry where there is an optical path taken by light that is incident from the object plane onto the front group and imaged on the image plane, and D3 is a length of the effective area of the first transmitting surface in a direction parallel to the axis of rotational symmetry where there is an optical path taken by light that is incident from the object plane on the front group and imaged on the image plane.

8. The optical system according to claim 1, wherein the first transmitting surface in the front group is convex on an object side and has a positive power.

9. The optical system according to claim 1, wherein at least one surface in the front group is defined by a rotationally symmetric free-form surface.

10. The optical system according to claim 7, wherein at least one surface in the front group is defined by a rotationally symmetric free-form surface.

11. The optical system according to claim 9, wherein at least one surface in the back group is defined by a rotationally symmetric free-form surface.

12. The optical system according to claim 10, wherein at least one surface in the back group is defined by a rotationally symmetric free-form surface.

13. The optical system according to claim 11, wherein the back group includes a transparent body both sides of which are defined by an extended rotational free-form surface.

14. The optical system according to claim 12, wherein the back group includes a transparent body both sides of which are defined by an extended rotational free-form surface.

15. The optical system according to claim 13, wherein the back group includes a cemented transparent body defined by cementing of two transparent bodies, each one having extended rotational free-form surfaces on both its sides.

16. The optical system according to claim 14, wherein the back group includes a cemented transparent body defined by cementing of two transparent pieces, each one having extended rotational free-form surfaces on both its sides.

17. An imaging apparatus comprising:
the optical system according to claim 1; and
an imaging device wherein a quantity of light for each pixel of an image formed through the optical system is converted into an electrical signal.

18. The imaging apparatus according to claim 17, further comprising:
an operating unit for operating the imaging apparatus;
a control unit for controlling the imaging apparatus based on a signal from the operating unit;
an image processor for processing an electrical signal from the imaging device to obtain an image; and
a recording unit for recording the obtained image.

19. An endoscope system comprising:
the imaging apparatus according to claim 17; and
a display unit for displaying the image.

20. A rangefinder system comprising:
the imaging apparatus according to claim 17; and
a range computation unit in which an image of an object of interest acquired by the imaging apparatus is subjected to image processing and then to computation processing to find a range to the object of interest.

* * * * *